United States Patent
Lees et al.

(10) Patent No.: US 9,888,995 B2
(45) Date of Patent: Feb. 13, 2018

(54) CATHETER-BASED APPARATUSES AND METHODS

(71) Applicant: Transverse Medical, Inc., Golden, CO (US)

(72) Inventors: Brad Lees, Sammamish, WA (US); J. Eric Goslau, Evergreen, CO (US); Michael K. Handley, Windsor, CO (US); Steven Wayne Berhow, St. Michael, MN (US); Douglas Scott Wahnschaffe, Monticello, MN (US); Reed Allan Houge, Buffalo, MN (US); David Schechter, Boulder, CO (US)

(73) Assignee: Transverse Medical, Inc., Fort Collins, CO (US)

(*) Notice: Subject to any disclaimer, the term of this patent is extended or adjusted under 35 U.S.C. 154(b) by 0 days.

(21) Appl. No.: 14/890,679

(22) PCT Filed: May 14, 2014

(86) PCT No.: PCT/US2014/000106
§ 371 (c)(1),
(2) Date: Nov. 12, 2015

(87) PCT Pub. No.: WO2014/185969
PCT Pub. Date: Nov. 20, 2014

(65) Prior Publication Data
US 2016/0100928 A1    Apr. 14, 2016

Related U.S. Application Data

(63) Continuation-in-part of application No. 13/894,910, filed on May 15, 2013.
(Continued)

(51) Int. Cl.
*A61F 2/01* (2006.01)
*A61F 2/24* (2006.01)

(52) U.S. Cl.
CPC ............ *A61F 2/013* (2013.01); *A61F 2/2427* (2013.01); *A61F 2002/016* (2013.01);
(Continued)

(58) Field of Classification Search
CPC ........................................ A61F 2/01–2002/018
(Continued)

(56) References Cited

U.S. PATENT DOCUMENTS

| 3,540,431 A | 11/1970 | Mobin-Uddin |
| 5,329,942 A | 7/1994 | Gunther et al. |

(Continued)

FOREIGN PATENT DOCUMENTS

| WO | 2008002871 A2 | 1/2008 |
| WO | WO2014076219 | 5/2014 |
| WO | 2014120509 A2 | 8/2014 |

OTHER PUBLICATIONS

Kereiakes, et al. "A Novel Filter-Based Distal Embolic Protection Device for Percutaneous Intervention of Saphenous Vein Graft Lesions Results of the AMEthyst Randomized Controlled Trial," JACC: Cardiovascular Interventions, vol. 1, No. 3, 2008, The American College of Cardiology Foundation, published by Elsevier, Inc.
(Continued)

*Primary Examiner* — Kathleen Holwerda
(74) *Attorney, Agent, or Firm* — Crawford Maunu PLLC

(57) ABSTRACT

Blood flow into vascular tissue is filtered in a manner that can also be useful for trapping particulates while allowing the flow of blood. Consistent with one or more embodiments, a filter apparatus includes a filter, an outer delivery sheath such as a catheter, and one or more shafts that are operable to manipulate the shape of the filter for positioning within vascular tissue. The filter conforms to various types of vascular tissue, and filters blood flow passing through
(Continued)

openings in the vascular tissue. In some implementations, the filter is used to trap particulates that have been collected on the filter, and collapses to trap and draw the particulates into the outer delivery sheath.

28 Claims, 16 Drawing Sheets

Related U.S. Application Data

(60) Provisional application No. 61/823,277, filed on May 14, 2013.

(52) U.S. Cl.
CPC ... *A61F 2002/018* (2013.01); *A61F 2230/008* (2013.01); *A61F 2230/0013* (2013.01); *A61F 2230/0095* (2013.01)

(58) Field of Classification Search
USPC .......................................................... 606/200
See application file for complete search history.

(56) References Cited

U.S. PATENT DOCUMENTS

| | | | |
|---|---|---|---|
| 5,769,816 A * | 6/1998 | Barbut | A61F 2/013 604/93.01 |
| 6,179,859 B1 | 1/2001 | Bates et al. | |
| 6,325,815 B1 * | 12/2001 | Kusleika | A61B 17/221 606/200 |
| 6,355,051 B1 * | 3/2002 | Sisskind | A61F 2/013 606/200 |
| 6,395,014 B1 | 5/2002 | Macoviak et al. | |
| 6,499,487 B1 | 12/2002 | McKenzie et al. | |
| 6,663,652 B2 | 12/2003 | Daniel et al. | |
| 6,843,798 B2 | 1/2005 | Kusleika et al. | |
| 7,083,633 B2 | 8/2006 | Morrill et al. | |
| 7,232,453 B2 | 6/2007 | Shimon | |
| 7,323,001 B2 | 1/2008 | Clubb et al. | |
| 7,585,309 B2 | 9/2009 | Larson | |
| 7,621,870 B2 * | 11/2009 | Berrada | A61F 2/013 600/200 |
| 7,785,343 B2 | 8/2010 | Johnson et al. | |
| 3,062,324 A1 | 11/2011 | Shimon et al. | |
| 8,114,114 B2 | 2/2012 | Belson | |
| 8,308,754 B2 | 11/2012 | Belson | |
| 8,414,482 B2 | 4/2013 | Belson | |
| 8,430,904 B2 | 4/2013 | Belson | |
| 8,460,335 B2 * | 6/2013 | Carpenter | A61F 2/013 606/200 |
| 8,679,149 B2 | 3/2014 | Belson | |
| 8,728,114 B2 | 5/2014 | Belson | |
| 9,107,734 B2 | 8/2015 | Belson | |
| 2002/0022858 A1 | 2/2002 | Demond et al. | |
| 2002/0161394 A1 * | 10/2002 | Macoviak | A61B 17/12136 606/200 |
| 2003/0100940 A1 * | 5/2003 | Yodfat | A61F 2/01 623/1.15 |
| 2003/0187475 A1 * | 10/2003 | Tsugita | A61F 2/01 606/200 |
| 2003/0199819 A1 | 10/2003 | Beck | |
| 2004/0073243 A1 | 4/2004 | Sepetka et al. | |
| 2004/0073253 A1 | 4/2004 | Morrill et al. | |
| 2004/0093015 A1 | 5/2004 | Ogle | |
| 2004/0215167 A1 | 10/2004 | Belson | |
| 2005/0119688 A1 * | 6/2005 | Bergheim | A61F 2/013 606/200 |
| 2005/0267516 A1 | 12/2005 | Soleimani et al. | |
| 2006/0025804 A1 | 2/2006 | Krolik et al. | |
| 2006/0190025 A1 | 8/2006 | Lehe et al. | |
| 2007/0185525 A1 | 8/2007 | White et al. | |
| 2007/0225750 A1 | 9/2007 | Ren et al. | |
| 2008/0140110 A1 | 6/2008 | Spence | |
| 2008/0195140 A1 | 8/2008 | Myla et al. | |
| 2010/0179583 A1 | 7/2010 | Carpenter et al. | |
| 2010/0179584 A1 | 7/2010 | Carpenter et al. | |
| 2010/0179647 A1 | 7/2010 | Carpenter et al. | |
| 2010/0211095 A1 | 8/2010 | Carpenter | |
| 2010/0305604 A1 | 12/2010 | Pah | |
| 2010/0324589 A1 | 12/2010 | Carpenter et al. | |
| 2011/0106134 A1 * | 5/2011 | Thompson | A61F 2/013 606/200 |
| 2011/0295304 A1 | 12/2011 | Jonsson | |
| 2013/0096606 A1 * | 4/2013 | Bruchman | A61F 2/013 606/200 |
| 2013/0123835 A1 | 5/2013 | Anderson et al. | |
| 2016/0100928 A1 * | 4/2016 | Lees | A61F 2/013 606/200 |

OTHER PUBLICATIONS

Lees et al. PCT Search Report & Opinion, USPTO, Application No. PCT/US2014/000106, dated Dec. 9, 2014.

* cited by examiner

CLOSED POSITION

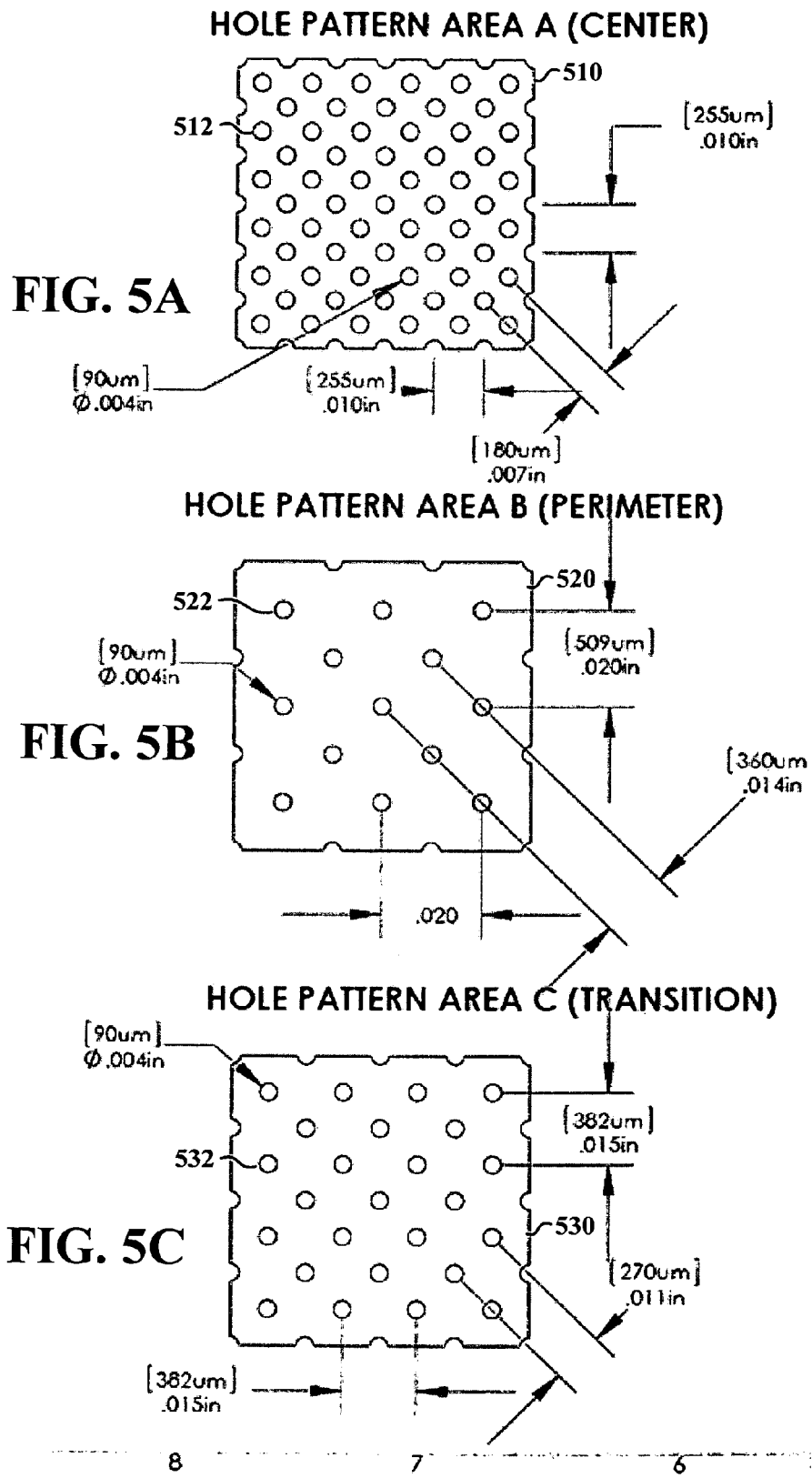

CATHETER-BASED APPARATUSES AND METHODS

FIELD

Aspects of various embodiments are directed to catheter-based apparatuses and methods therefor.

BACKGROUND

Various treatments can be useful for treating a variety of medical conditions, such as coronary heart disease, aneurysm and others. These treatments can often involve intervention with tissue, such as to remove, repair or otherwise treat tissue. For instance, coronary heart disease can sometimes involve heart valve disorders, which can be addressed via intervention techniques in which valves are repaired or replaced.

One manner that has been useful for treating various conditions involves the use of a catheter to enter a patient's arteries and provide access for a variety of techniques. For instance, various procedures can be performed via catheters, such as to repair or remove tissue, or to implant tissue or other devices. One such approach for addressing heart disease involves transcatheter-aortic valve replacement or implementation therapies (TAVR/TAVI). These and other trans-vascular approaches may involve the delivery of artificial or animal flaps/valves to a patient's heart via catheters.

While many treatment approaches have been useful, there have been many challenges to their safe implementation. It is common to introduce, cross and exchange a variety of percutaneous devices such as guide wires, catheters, sheaths, guide catheters, and adjunctive technologies to gain access to and treat a coronary vessel, coronary valve, or other vascular anatomy. These and other approaches to the repair or replacement of tissue can dislodge particles/debris (emboli) which are freed (released) from the vessel walls and structures causing uncontrolled and unprotected floating emboli to move freely. This freed emboli, and freely floating and uncontrolled emboli can be carried distally (away) via the blood stream and cause issues, such as by blocking or occluding coronary, peripheral, and neurovascular vessels. For instance, during the (TAVR/TAVI) procedure, native tissue can be compressed into the aorta wall to make room for replacement devices. This action may cause dislodging or displacement of arterial plaque, calcium, or thrombus as the devices transverse the aortic arch. These particles can have adverse effects, such as by causing a stroke. These and other matters have presented challenges to a variety of treatment approaches.

SUMMARY

Various example embodiments are directed to catheter-based apparatuses and their implementation.

According to an example embodiment, an apparatus includes an outer catheter extending from a proximal end to a distal end, first and second shafts, and a filter. The first shaft extends through the catheter from the proximal end to the distal end, moves within the outer catheter, and has an end portion that retracts within the proximal end. The second shaft extends through the outer catheter, moves relative to the first shaft and has an end portion that extends beyond the end portion of the first shaft, in which at least a portion of the second shaft retracts into the outer catheter. The filter passes human red blood cells and mitigates the passage of particles having a dimension larger than the human red blood cells. The filter has a perimeter structure that is connected to or part of the second shaft and operates with the first and second shafts to: expand to a first state in response to a portion of the second shaft being in a first position relative to the first shaft, with the filter having a dimension that is wider than a cross-sectional area of the outer catheter when in the first state; and collapse to a second state in response to the second shaft being manipulated relative to the first position, with the filter and outer catheter being operative to facilitate retraction of the filter into the outer catheter in the second state.

Another embodiment is directed to a method as follows. The distal end of an outer catheter is deployed into vascular tissue, with outer catheter extending from a proximal end to a distal end and including first and second shafts, and a filter. The first shaft is within the outer catheter, has an end portion that retracts within the proximal end, extends through the catheter from the proximal end to the distal end and operates to move within the outer catheter. The second shaft extends through the first shaft and the outer catheter and is operative to move within the first shaft and retract at least partially therein, and has an end portion that extends beyond the end portion of the first shaft. The filter has a perimeter structure that is connected to the second shaft and passes human red blood cells and mitigates the passage of particles having a dimension larger than the human red blood cells. The first and second shafts are manipulated relative to one another to: expand the filter to a first state by positioning a portion of the second shaft in a first position relative to the first shaft, with the filter having a dimension that is wider than a cross-sectional area of the outer catheter in the first state; in the first state, use the filter to pass human red blood cells and to mitigate the passage of particles having a dimension larger than the human red blood cells, collapse the filter to a second state by extending the second shaft being from the first position to a second position in which the second shaft extends further out of the first shaft, relative to the first position. In the second state, the first shaft is moved relative to the outer catheter to retract the filter into the outer catheter.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIGS. 1A-1D show a catheter apparatus, in accordance with one or more example embodiments of the present disclosure, in which FIG. 1A shows an overview of the apparatus, FIG. 1B shows a filter of the apparatus in a collapsed position, FIG. 1C shows a sectional view of the filter in an expanded position, and FIG. 1D shows a sectional view of the filter in the collapsed position;

FIGS. 3A-3E show an implementation of a catheter apparatus, in accordance with one or more embodiments, in which FIG. 3A shows a catheter apparatus inserted at an aortic arch, FIG. 3B shows the catheter apparatus with a filter therein deployed in a collapsed state, FIG. 3C shows the catheter apparatus with the filter deployed in an expanded state, FIG. 3D shows the catheter apparatus with the filter deployed in the expanded state and having particles captured therein, FIG. 3E shows the catheter apparatus with the filter in the collapsed state with particles trapped therein and being withdrawn into an outer catheter sheath.

FIGS. 5A-5C show portions of respective filter material, as may be implemented in connection with one or more embodiments;

Figure 1A:
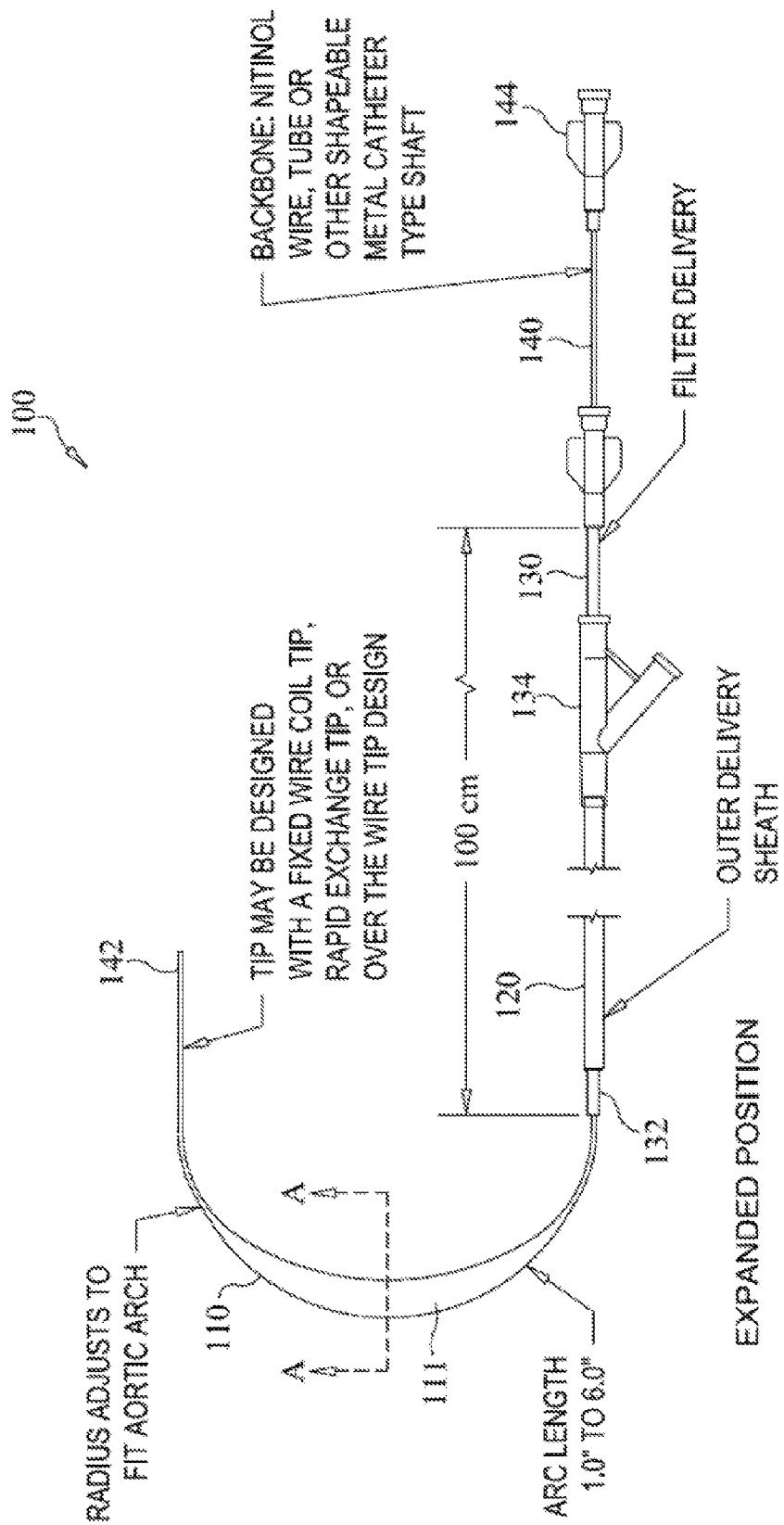

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving catheter-based apparatuses and methods. While not necessarily so limited, various aspects may be appreciated through a discussion of examples using this context.

Various example embodiments are directed to filtering blood flow into vascular tissue, which can be useful for trapping particulates while allowing the flow of blood. In a particular embodiment, a filter apparatus includes an outer delivery sheath (e.g., a catheter) with single or multi-lumens/shafts facilitate deployment, positioning and retraction of a filter that filters the blood flow. The apparatus is operative to conform the filter to a variety of types of vascular tissue and, therein, to filter blood flow passing through openings in the vascular tissue under normal blood flow conditions. In some implementations, the filter is used to trap particulates that have been collected on material thereof, and to draw the trapped particulates into the outer delivery sheath for removal.

Another embodiment is directed to an apparatus having an outer catheter extending from a proximal end to a distal end, first and second shafts, and a filter. The first shaft extends through the catheter from the proximal end to the distal end and moves within the outer catheter, with an end portion that retracts within the proximal end. The second shaft (e.g., a wire or filament) extends through the outer catheter and moves relative to the first shaft. The second shaft has an end portion that extends beyond the end portion of the first shaft (e.g., beyond an intermediate end portion of the first shaft that retracts into the outer catheter), with some of or the entire second shaft being retractable into the outer sheath. The filter passes human red blood cells and mitigates the passage of particles having a dimension larger than the human red blood cells. A filter perimeter structure is connected to or part of the second shaft, such that the filter expands to a first state in response to a portion of the second shaft being in a first position relative to the first shaft (e.g., therein bowing the perimeter structure outward), with the filter having a dimension in the first state that is wider than a cross-sectional area of the outer catheter. The perimeter structure collapses the filter to a second state in response to the second shaft being manipulated to a second position, relative to the first shaft. In one such instance, the perimeter structure has an end portion connected to the first shaft, and responds to retraction into the outer sheath by collapsing the filter so that it can be retracted into the outer catheter with particles trapped therein.

In another embodiment, the aforementioned apparatus includes a shaft or backbone type structure that extends through the catheter (e.g., as may be integrated with the first shaft). The second shaft includes a fixed portion (e.g., part of the perimeter) connected to the backbone and operates therewith to expand the filter to the first state in response to a movable portion of the second shaft being extended toward the fixed portion of the second shaft. Further, the second shaft and backbone collapse the filter to the second state in response to the movable portion of the second shaft being retracted away from the fixed portion of the second shaft.

In some implementations, the filter or other filters as described herein have a porous material that exhibits variations in porosity at different portions of the filter. In one such implementation, a first filter portion has a first porosity that facilitates conformation to vessel sidewalls in response to fluid pressure, and a second filter portion has a second porosity that is higher than the first porosity (e.g., more readily passes fluid). In operation, the second portion passes red blood cells through openings in sidewalls of a vessel to which the first portion is conformed. As such, by aligning the filter to the vessel, portions of the filter having a lower porosity operate to apply a relatively high pressure to vessel sidewalls, while other portions of the filter aligned to openings in the sidewall readily pass red blood cells (and other fluid) with relatively lower pressure than that applied to the sidewalls. Such an approach may also facilitate deflection of the higher-porosity regions into the openings, readily sealing the openings with the filter such that most or all fluid passing into the openings passes through the filter. In some implementations, the filter includes one or more markers that help to identify the variations in porosity and therein align the filter to the openings.

In another embodiment, a secondary frame is connected to the second shaft and to the filter, and operates to shape the filter as a dome-type shape in which the perimeter forms an exposed edge of the dome. The secondary frame may, for example, be connected to the first shaft and to the filter, and operable to support the filter upon expansion thereof via the perimeter, such as by supporting a domed portion of the filter extending away from the exposed edge.

In another more specific embodiment, the filtering is effected using a backbone/shaft type structure extending through the outer delivery sheath and supporting the filter material. Manipulation of the backbone/shaft type structure relative to the outer delivery sheath effects shaping of the filter material and conforming of the filter material to vascular tissue. In some implementations, the backbone/ shaft type structure is movable within an inner shaft that also moves relative to the outer delivery sheath, with a distal end of the filter material being coupled to the backbone/shaft and a proximal end of the filter material being coupled to the inner shaft. In this context, movement of the backbone/shaft relative to the inner shaft causes expansion/collapse of the filter material, which can be used for deployment, conformation, and/or trapping of particles. Moreover, conforming the filter material in this manner can facilitate placement of the material near the wall of vascular tissue and out of higher blood flow regions central to the tissue, and thus facilitate maintaining coupling of the filter material to the sidewall.

The apparatuses and methods described herein may be implemented for a variety of procedures. Various such embodiments are directed to the field of embolic protection of the various vascular beds during coronary, vascular, and peripheral percutaneous interventions, trans-catheter, or trans-apical, or surgical procedures. Some embodiments are directed to a protection/capture device, which can be implemented with or without an all-inclusive delivery system, capture mechanism, and or retrieval device. This device may operate to protect, capture, aspirate, and/or deflect micro and macro emboli from traveling into or down vessels and vessel side branches while still maintaining adequate blood flow. Delivery and retrieval may be via percutaneous methods or surgical cut downs, or femoral access, brachial, radial, trans-apical, trans-catheter, or other methods. One or more such embodiments is directed to an embolic protection device that is conformable to anatomical structure of human aortic arches, and/or the anatomical structures and anomalies in other vascular structures, and provides protection to one or more branches. These approaches can be implemented to capture, filter, and/or trap embolic material from entering side branches of the vessels being treated by percutaneous catheters or other invasive technologies.

A more particular embodiment is directed to an apparatus having an outer catheter extending from a proximal end to a distal end (e.g., for insertion into human vascular tissue), first and second shafts that extend through the catheter and move relative to one another. The apparatus also includes a filter connected to a distal end of the second shaft, at the distal end of the catheter, and that passes human red blood cells while mitigating the passage of other larger particles (e.g., larger than red blood cells, or larger than white blood cells). The second shaft has an end portion that extends beyond the end portion of the first shaft, and retracts at least partially into the first shaft to manipulate the shape of the filter. The first shaft also retracts into the catheter, with the first shaft and the filter. In some embodiments, the second shaft extends along a central portion of the filter.

The filter has a perimeter structure, such as a frame, filter mesh, or one or more retractable backbone/shaft-type structures, and that is connected to the second shaft for expanding and collapsing the filter between first and second states, based upon a relative position of the first and second shafts. The filter operates with the first and second shafts to expand to a first state when the second shaft is in a first position relative to the first shaft, and collapses to a second state when the second shaft is in a second, extended position relative to the first shaft. The filter has a dimension that is wider than a cross-sectional area of the outer catheter when in the first state, and is retractable into the catheter when in the second state.

In accordance with the above and/or other catheter-based embodiments, one or more such aspects may be implemented with and/or using one or more embodiments in U.S. Provisional Application Ser. No. 61/647,283, filed on May 15, 2012, and/or in U.S. Provisional Application Ser. No. 61/823,277, filed on May 14, 2013, both of which are fully incorporated herein by reference.

In a more particular embodiment, the filter has first and second end portions respectively connected to the end portions of the first and second shafts, and operates to change in shape, expand and collapse based upon relative movement of the end portions as controlled via relative movement of the first and second shafts. The filter may include one or more of a variety of materials as discussed herein, such as a semi-permeable membrane, fabric or fiber mesh.

In this context, the filter is expanded by causing respective portions of the perimeter structure, at edges of the filter and on opposite sides of the shaft, to spread apart from one another. This expansion may, for example, be implemented to conform the filter to a sidewall of vascular tissue such as an aortic arch, and cover an opening into at least one artery connected to the vascular tissue. Moreover, the expansion and manipulation of the filter may be implemented to cover one or more arteries in a variety of aortic arch configurations, such as may include 2, 3, 4 arteries coupled to the aortic arch.

The filter is collapsed by causing the respective portions of the perimeter structure to curl and overlap, and in some implementations, is collapsed as such to trap filtered particles therein (e.g., for removal via the catheter). This removal may, for example, involve trapping a preponderance (at least half) of the particles that are in contact with the filter when the filter is collapsed to the second state. In another example, this removal involves trapping substantially all particles (e.g., at least 90%) in contact with the filter when the filter is collapsed.

Filters as described herein are conformed to vascular tissue in one or more of a variety of manners. In some embodiments, the filter has opposing surfaces and operates with first and second shafts as above to conform to the wall of vascular tissue and cover at least one opening therein. Substantially all of one of the surfaces of the filter is either in contact with the wall or extends over the at least one opening with portions of the filter being in contact with the wall immediately adjacent the opening. In some implementations, the first and second shafts are operative to adjust a radius of the filter via relative movement of the shafts, to effect such conformity. In other implementations, the first and second shafts incrementally manipulate the shape of the perimeter structure based upon the relative position of the first and second shafts. Other implementations are directed to the use of further shafts with the filter, to adjustably shape the filter to conform to specific vascular tissue. In some embodiments, the perimeter of the filter is implemented with a flexible frame or flexible matrix that extends along the perimeter of the filter and operates to facilitate such shaping.

In various embodiments, a filter as discussed herein includes a mesh density or other porosity-related aspect that operates to conform the filter to a sidewall, such as a sidewall of the ostium of the great vessels of a human being, via flow restriction characteristics of the filter. In some implementations, the filter has respective portions exhibiting different flow restriction (e.g., as related to porosity) characteristics in different regions, with a conforming region or regions exhibiting relatively high flow restriction that utilizes fluid pressure to conform those conforming to the sidewall, and a fluid-passing region or regions exhibiting a relatively lower flow restriction that permits fluid (e.g., including red blood cells) to pass through the filter and into openings in the sidewall. In some implementations, the fluid-passing region(s) operate to conform to the sidewall at portions thereof intersecting with the openings, and further extend into the openings.

Various such vessel-conforming approaches may, for example, be amenable to applications in which the filter conforms to the aforementioned sidewall of the ostium of the great vessels in response to blood pressure upon conforming regions that conform to the sidewall, and in which fluid-passing regions of the filter cover and deflect into the great vessels in response to pressure of fluid passing through the fluid-passing regions. In a particular embodiment, the density of the filter provides at least 20%, such as more than 27%, coverage of sidewall openings with pore various sizes (e.g., ranging from 90 to 110 microns), with a pore size lower limit being operable to mitigate or prevent disruption of hemodynamics and facilitate desirably low pressure drop across the filter (for blood flowing through and into the great vessels).

In various embodiments, the filter is positioned with relative porosity characteristics being implemented with respective sidewall and sidewall opening regions. For instance, by placing a radiopaque marker or markers on portions of the filter to identify various porosity type characteristics thereof, the markers can be used to position the filter such that regions of lower porosity used to conform the filter to a sidewall are positions away from and/or not covering openings in the sidewall, while portions of higher porosity are aligned with such openings to pass fluid therewith.

Various embodiments are directed to the passage of fluid between proximal and distal ends of the catheter, such as to deliver drugs or to aspirate. Accordingly, one or more of the first and second (or other) shafts are operative with openings therein to pass fluid, or one or more of the respective shafts are implemented to provide for such fluid flow between the shafts. In a particular embodiment, anti-coagulant is delivered from the proximal end of the catheter and onto the filter, and is used to disperse the anti-coagulant along the filter and mitigate collection of red blood cells. In another embodiment the filter includes (e.g., is impregnated with) one or more of an anticoagulant that mitigates collection of red blood cells in the filter, and an attractant that facilitates coupling of the filter with particles carried by fluid passing through the filter.

Another embodiment is directed to a method as follows. The distal end of an outer catheter as described above is deployed into vascular tissue, with outer catheter extending from a proximal end to a distal end and including first and second shafts, and a filter. The first and second shafts are manipulated relative to one another to control the filter's shape. The filter is thus expanded to a first state by positioning a portion of the second shaft in a first position relative to the first shaft, with the filter having a dimension that is wider than a cross-sectional area of the outer catheter in the first state. The filter is used in the first state to pass human red blood cells and to mitigate the passage of particles having a dimension larger than the human red blood cells (e.g., larger than white blood cells). The filter is collapsed to a second state by extending the second shaft further out of the first shaft, relative to the first position, after which the first shaft is moved to retract the filter (and any particles trapped as described above) into the outer catheter.

Figure 1B:
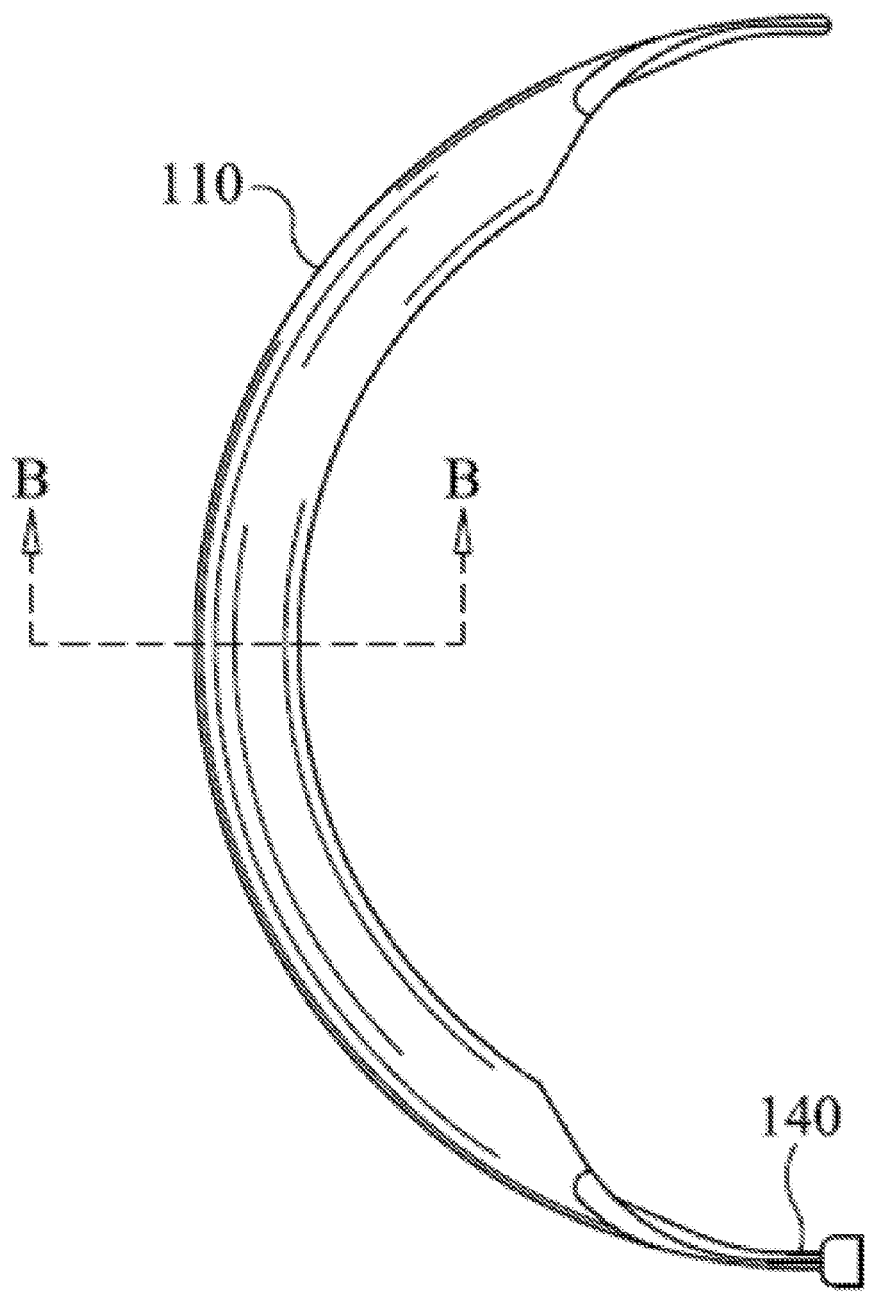

Turning now to the figures, FIGS. 1A-1D show a catheter apparatus 100, in accordance with one or more example embodiments of the present disclosure. Beginning with FIG. 1A, the apparatus 100 includes a filter device 110 that is deployed via an outer catheter 120, and which includes a filter material 111 such as a mesh, fabric or other semipermeable material. A first shaft 130 is movable within the catheter 120, and extends from a proximal end to a distal end 132 near the filter device 110. A second (backbone-type) shaft 140 passes through the first shaft 130, extending from a proximal end at 144 to a distal end 142, and is movable within the first shaft 130 for extending and retracting the filter device 110 out of and into the first shaft, and for rotating the filter device when deployed or deploying. The filter material 111 is shown in an expanded state in FIG. 1A, while FIG. 1B shows the filter material in a collapsed position/state in which the second shaft 140 is extended from the first shaft 130 to facilitate the collapse.

In this context, the catheter 120 can be inserted into a patient, such as via a femoral artery, and moved into a variety of vascular tissue locations, such as within an aortic arch as described herein and shown in other figures. Once in position, the first shaft 130 can be extended out of the catheter 120 to deploy the filter device 110. The filter device 110 is connected to the first shaft near the distal end 132 and also connected to the second shaft near distal end 142. The second shaft is operative to control movement and shape of the filter device (e.g., extending the second shaft further out of the first shaft collapses the filter material 111, and partially retracting the second shaft into the first shaft expands the filter material). The first shaft is also operative to rotate the filter device 111 as needed.

Figure 1C:
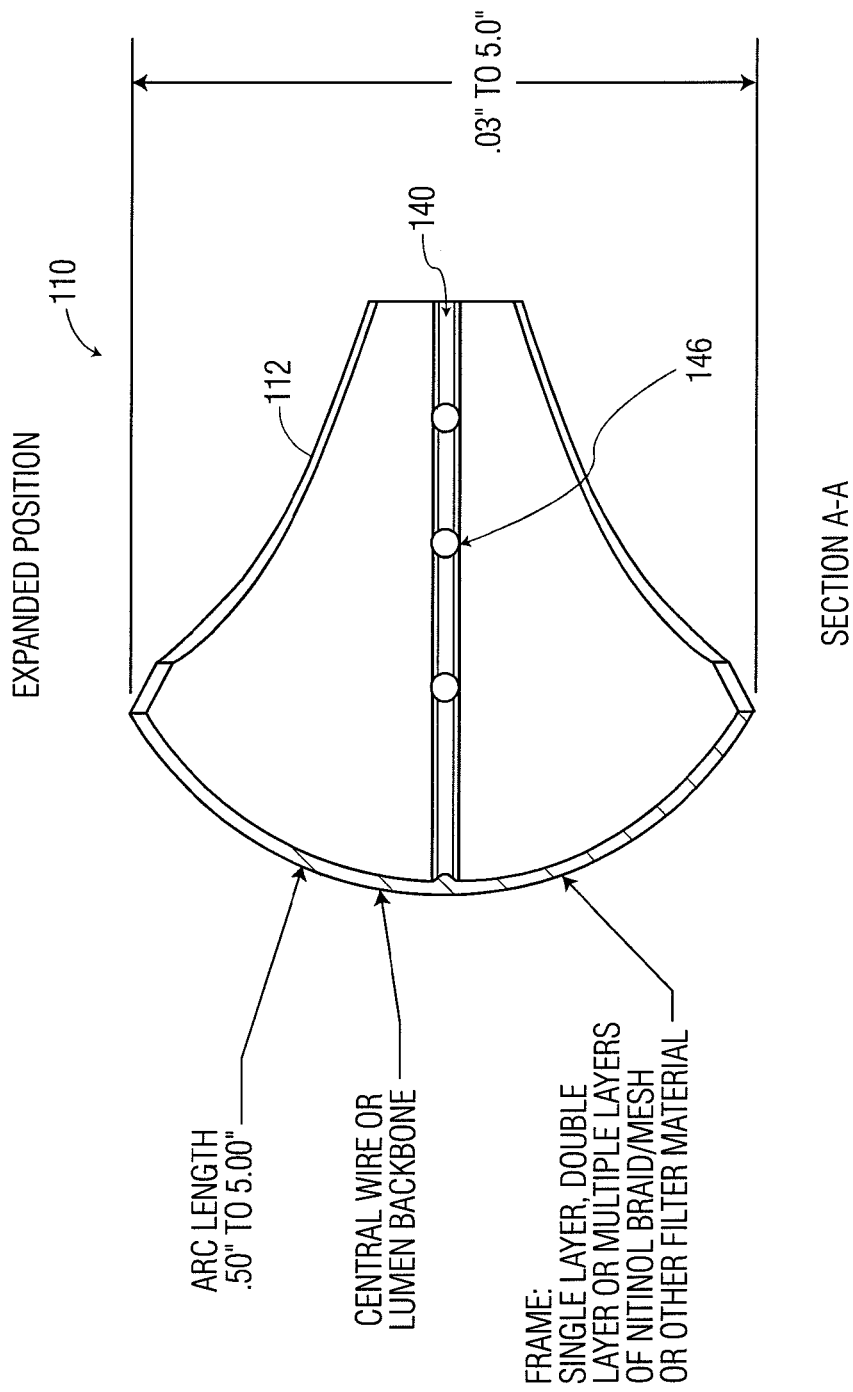
Figure 1D:
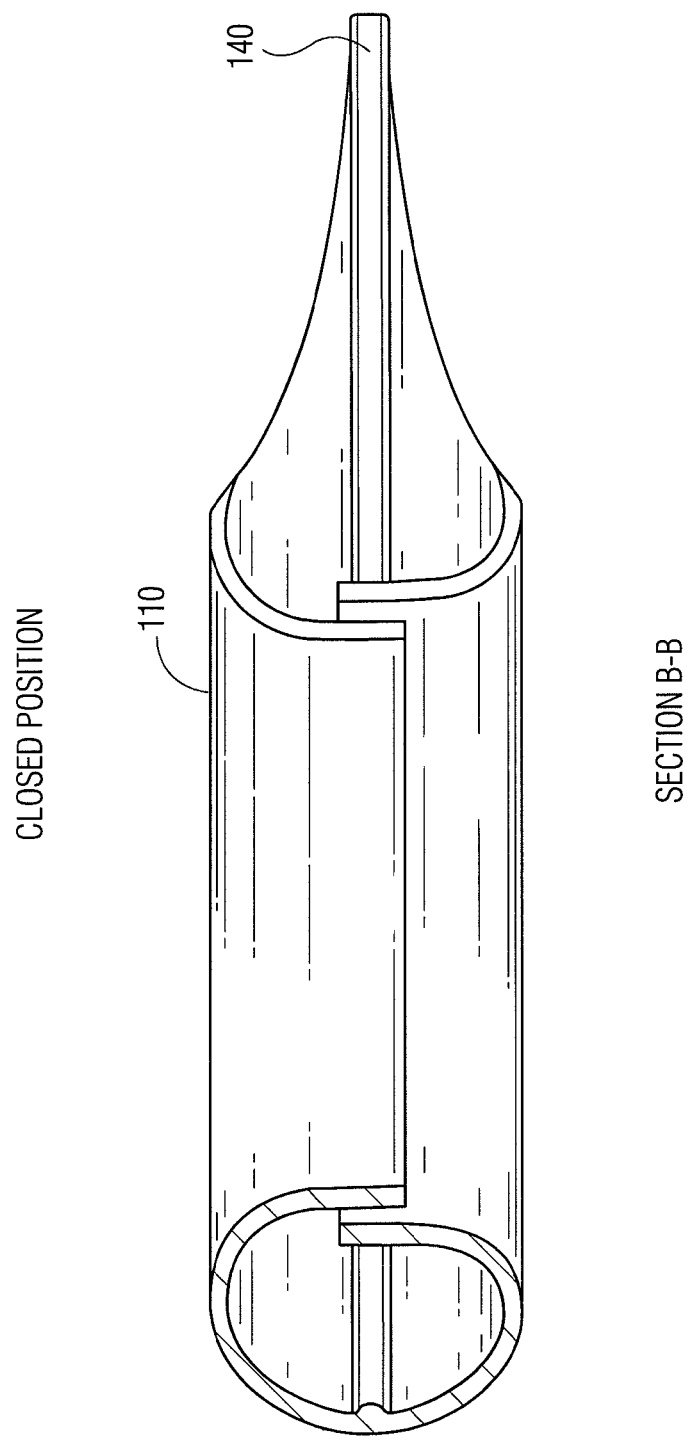

The apparatus 100 may be implemented using one or more of a variety of approaches, as consistent with the various embodiments discussed herein. FIGS. 1B-1D show various such embodiments as described in connection with FIG. 1A. Further, while FIG. 1A shows exemplary characteristics such as arc length, radius, tip structure and material types, these are by way of example and may be implemented using other materials and characteristics. For instance, certain embodiments are directed to implementation of the apparatus 100 for specific applications, such as for adult, child, infant or animal patients, or for implementation with specific types of vascular (other) tissue, with sizes adjusted accordingly.

In some implementations, the apparatus 100 is operative to facilitate fluid exchange via the catheter 120, such as for the delivery of drugs or other treatment, or for aspiration. By way of example, a fluid exchange (delivery/aspiration) connection 134 is shown for delivering fluid within the catheter and along the shaft first 130. Other embodiments are directed to fluid delivery internally via one or both of the first and second shafts 130 and 140. One such embodiment is directed to the delivery of fluid through the second shaft 140, as applied at the proximal end 144.

FIG. 1C shows a cross-sectional view "A-A" of the filter device 110 from FIG. 1A, with the filter material 111 being in an expanded position/state, while FIG. 1D shows a cross-sectional view "B-B" of the filter 110 in the collapsed position/state. In FIG. 1C, the second shaft/backbone 140 extends along a central portion of the filter material 111, with a perimeter structure 112 facilitating the expansion. The perimeter may, for example, include a hard wire type perimeter, or a portion of the filter material 111, which facilitates expansion and collapse of the filter material. By way of example, openings 146 in the second shaft 140 may be implemented to deliver fluid between the proximal and distal ends of the apparatus 100, such as to deliver anti-coagulating material to the filter material 111 to mitigate collection of red blood cells and promote the flow of the cells through the filter material. In FIG. 1D, the filter material 111 has been collapsed onto itself, with outer perimeters on opposing sides of the filter material being rolled over onto one another.

Figure 2:
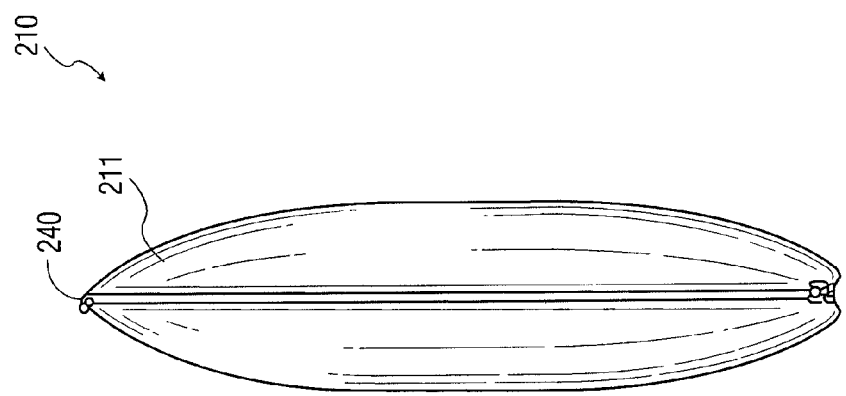
FIG. 2 shows a filter apparatus, in accordance with another example embodiment of the present invention.

FIG. 2 shows a filter apparatus 210, in accordance with another example embodiment of the present invention. The filter apparatus 210 includes a filter material 211 and a central backbone 240, and may be implemented in connection with the components shown and similarly-labeled in FIG. 1A. For instance, the second shaft 140 may operate as the backbone 240, with the filter apparatus 210 being implemented with apparatus 110, and the filter material 211 being expanded or collapsed as discussed above.

Figure 3A:
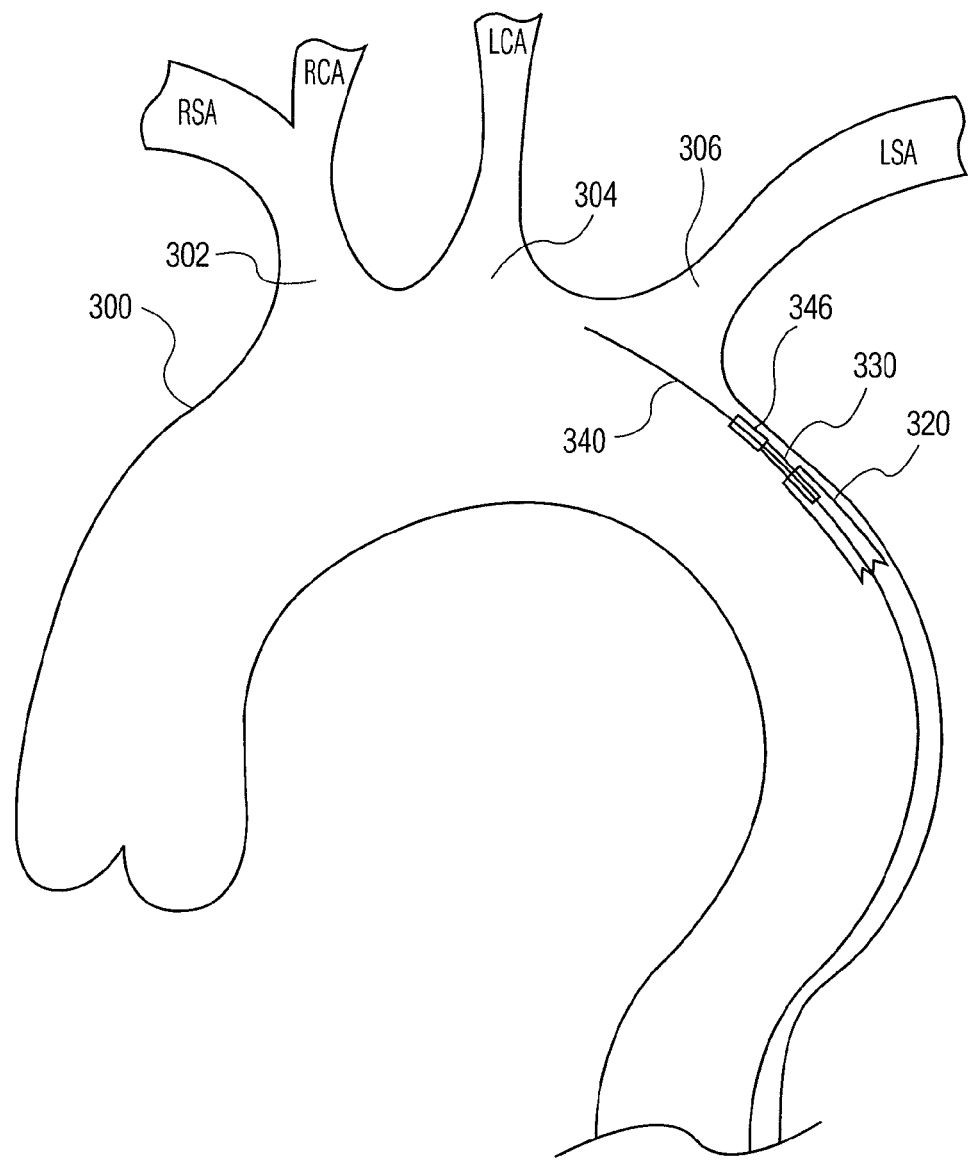

FIGS. 3A-3E show an implementation of a catheter apparatus, in accordance with one or more embodiments involving one or both of an apparatus and method therefor. The approaches shown in FIGS. 3A-3E may, for example, be implemented in connection with a catheter device similar to that shown in FIG. 1A. Referring to FIG. 3A, a catheter apparatus including an outer catheter 320, a first shaft 330 and a second shaft 340 is inserted at an aortic arch 300. The aortic arch is shown having respective arterial openings 302, 304 and 306 that are desirably covered during procedures, such as a transcatheter-aortic valve replacement or implementation (TAVR/TAVI) procedure.

Figure 3B:
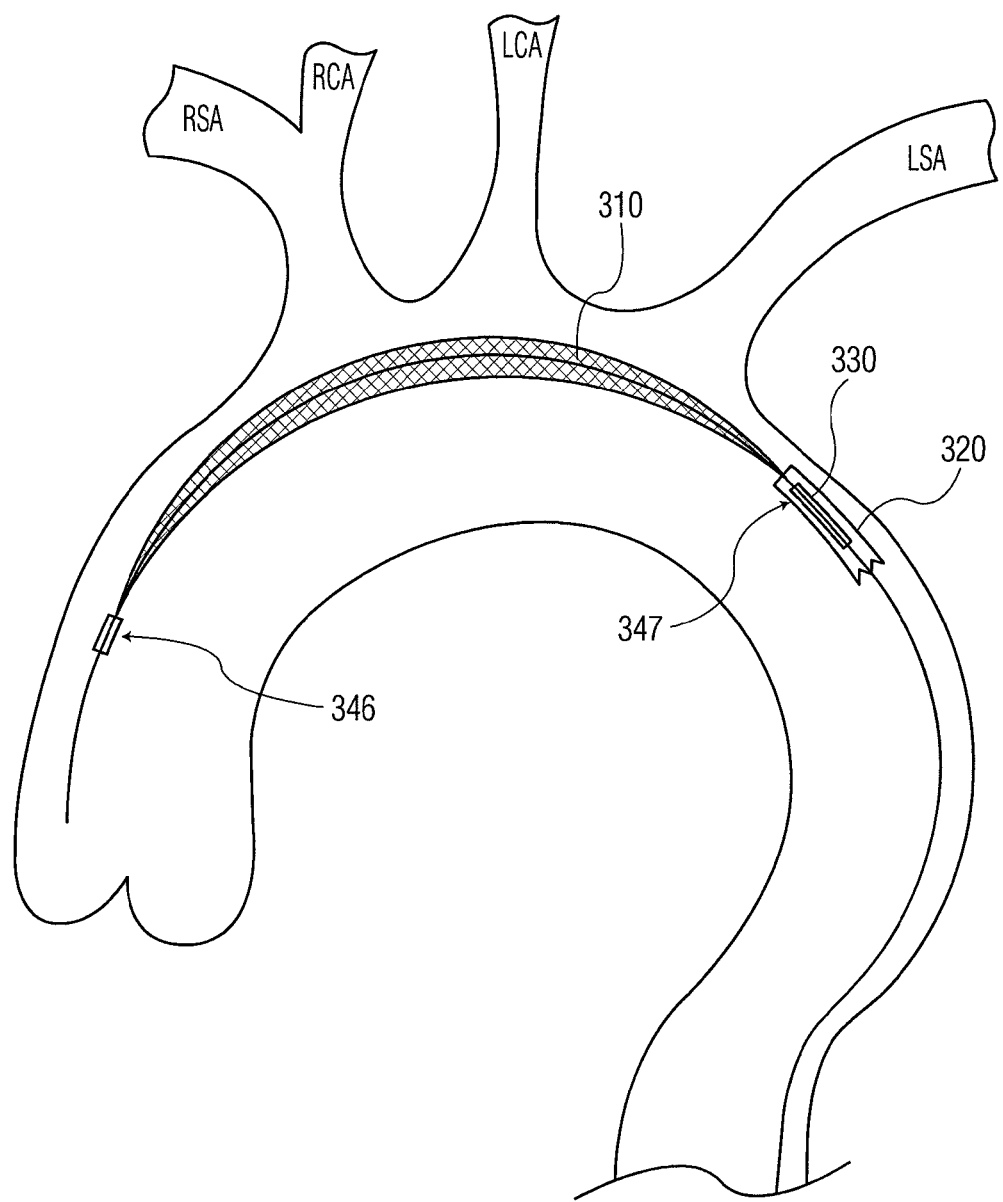
Figure 3C:
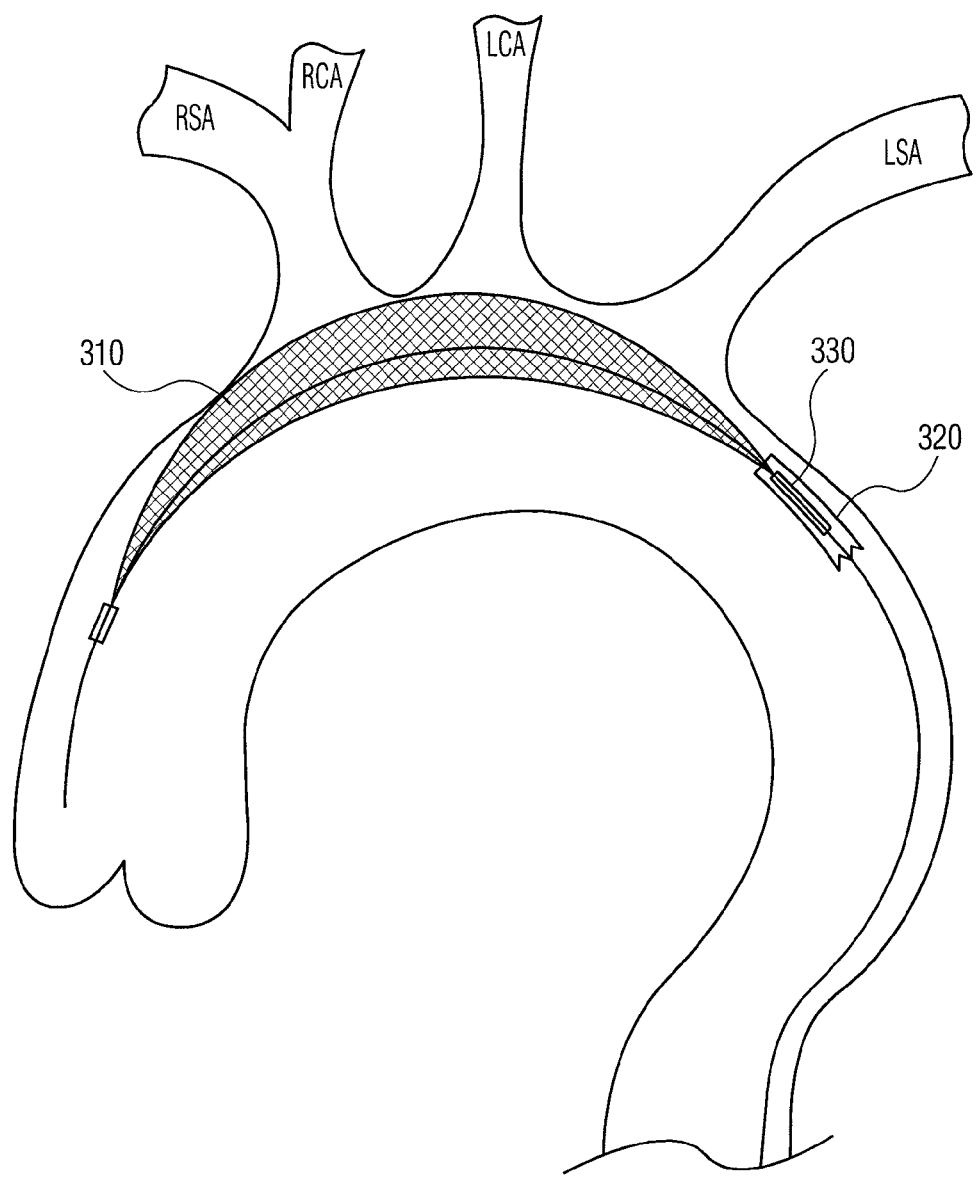
Figure 3D:
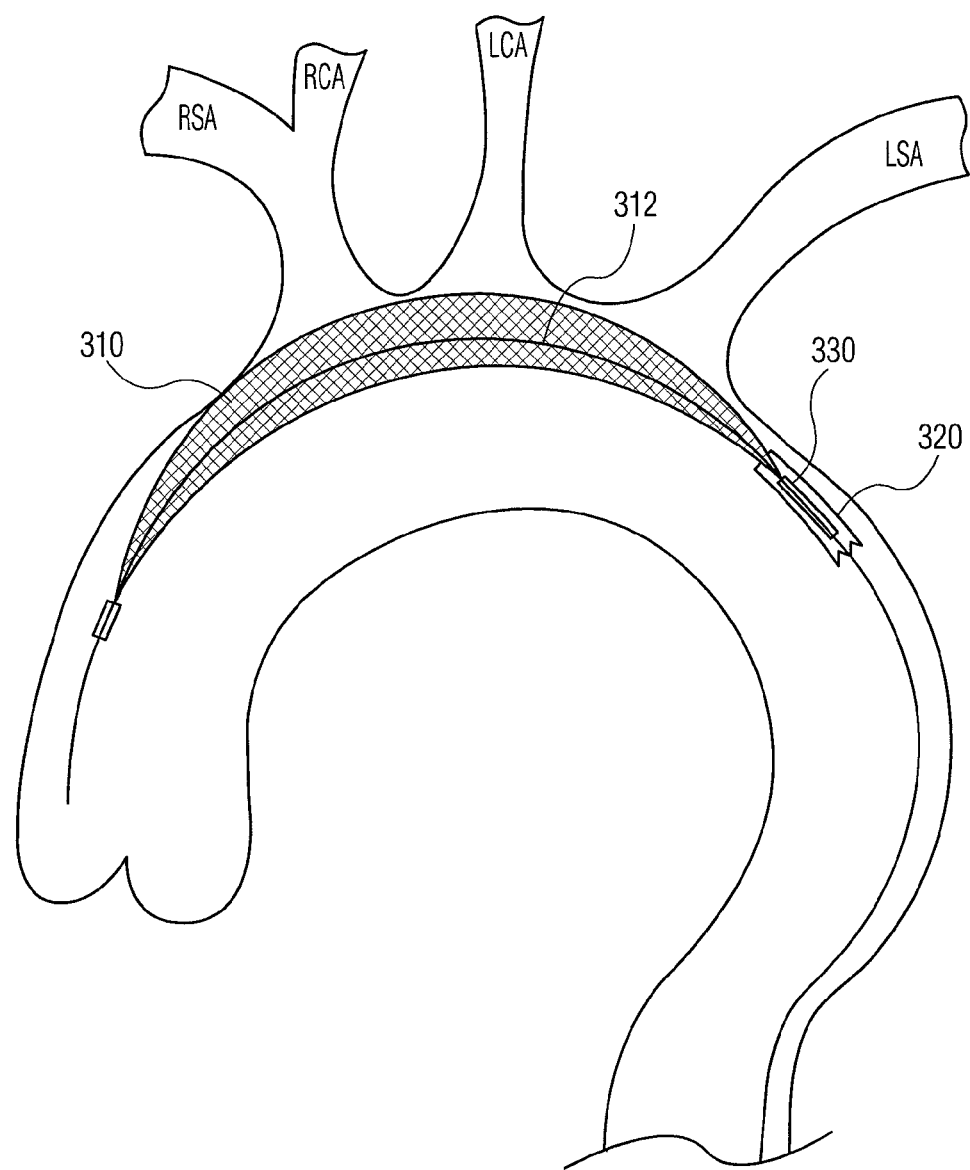

FIG. 3B shows the catheter apparatus with a filter 310 therein deployed in a collapsed state. Respective markers 346 (also shown in FIG. 3A) and 347 are used to provide an indication of the position of the filter 310. In FIG. 3C, the catheter apparatus is shown with the filter 310 deployed in an expanded state, covering openings 320, 304 and 306. In this expanded state, the filter 310 can be manipulated and conformed to sidewalls of the aortic arch 300, effectively covering the openings and forcing blood flow into the openings through a filter material of the filter 310. Once in place, the filter 310 operates to filter the blood flow, allowing passage of red blood cells while mitigating the passage of other particulates, such as may be dislodged or freed during a procedure. In this context, FIG. 3D shows the catheter apparatus with the filter deployed in the expanded state and having particles captured therein.

In some implementations, the filter 310 includes a material that mitigates collection or coagulation of red blood cells on the filter, which may otherwise inhibit the flow of blood into the openings 302, 304 and/or 306. This may be implemented using an approach such as shown with openings 146 shown in FIG. 1C, to deliver anti-coagulation materials to the filter material. In other implementations, the filter 310 includes material that attracts and traps/collects particulates, preventing the particulates from passing through the filter and into the openings 302, 304 and 306. Further, some implementations are directed to the use of both mitigation of the collection of red blood cells and attraction of other particles.

Figure 3E:
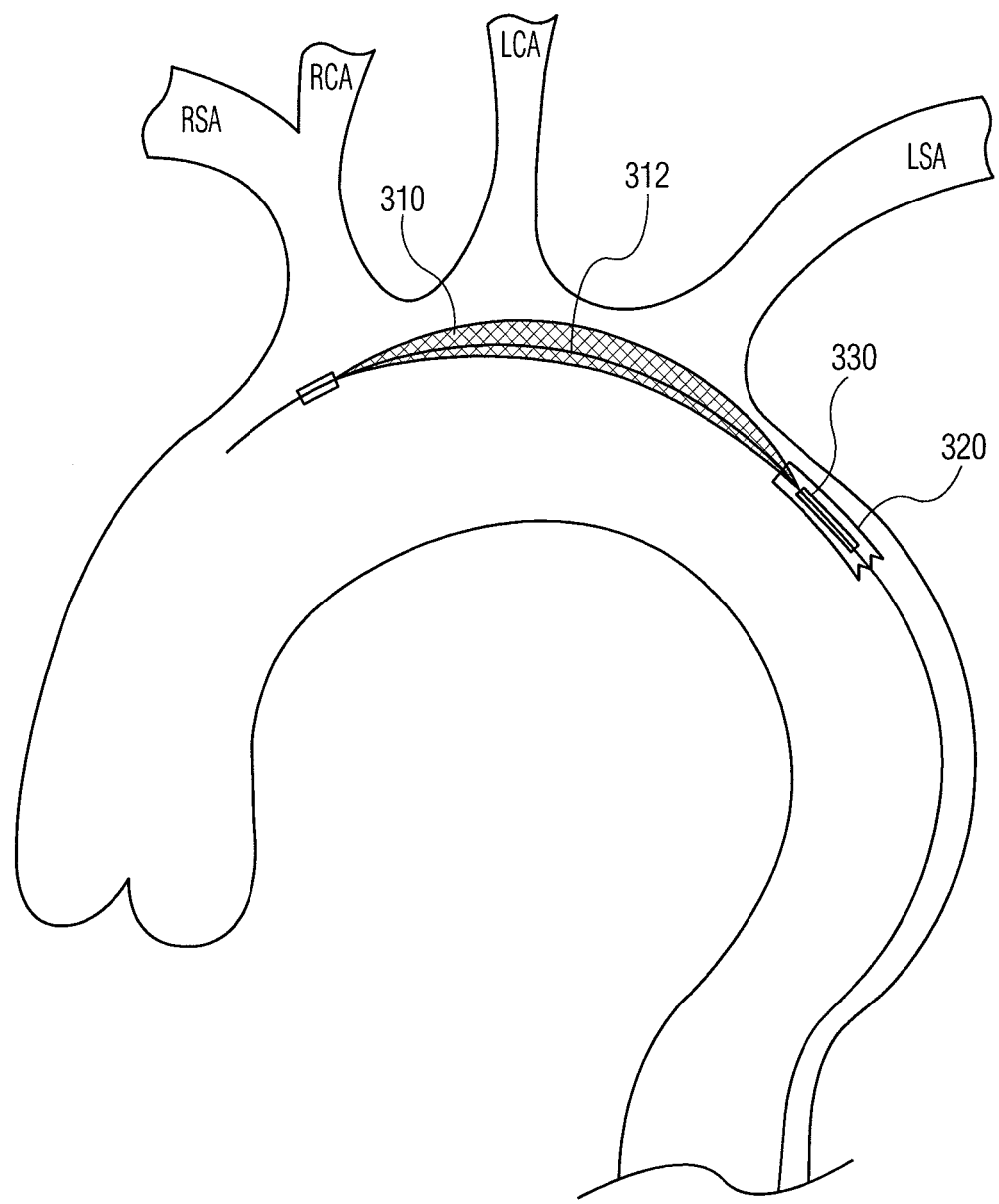

After a procedure is complete, the catheter apparatus is retracted into the outer catheter 320 as shown in FIG. 3E. The backbone 340 is manipulated to collapse the filter material, such as shown in FIGS. 1B and 1D, to trap the particles shown in FIG. 3D. Once collapsed, the filter apparatus 310 is retracted into the outer catheter 320 via movement of the first shaft 330 relative to the outer catheter 320. Once withdrawn into the outer catheter, the particles are trapped within both the filter 310 and the outer catheter, and can be safely removed.

Figure 4A:
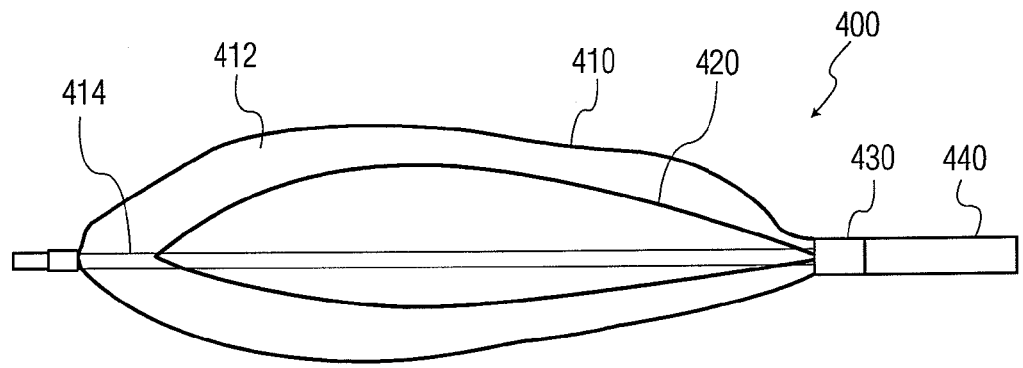
FIGS. 4A-4F show another catheter type apparatus at various stages of deployment, in accordance with one or more embodiments.

FIGS. 4A-4F show another catheter type apparatus 400 at various stages of deployment, in accordance with another embodiment. In FIG. 4A, the apparatus 400 is shown in an expanded state, with a perimeter wire 410 (and optional support wire 420) being extended relative to a shaft 430 and out of a sheath 440. For implementations including the support wire 420, some embodiments involve a coupling 414 between the perimeter wire 410 and the support wire 420 (e.g., a solid wire, crimped wire pair or twisted wire pair that may provide a continuous wire connection between the perimeter wire 410 and the support wire 420). In this expanded state, a filter 412 is coupled to the perimeter wire and operable for conforming to a vessel wall while also passing fluid through openings in the wall, such as described above.

Figure 4B:
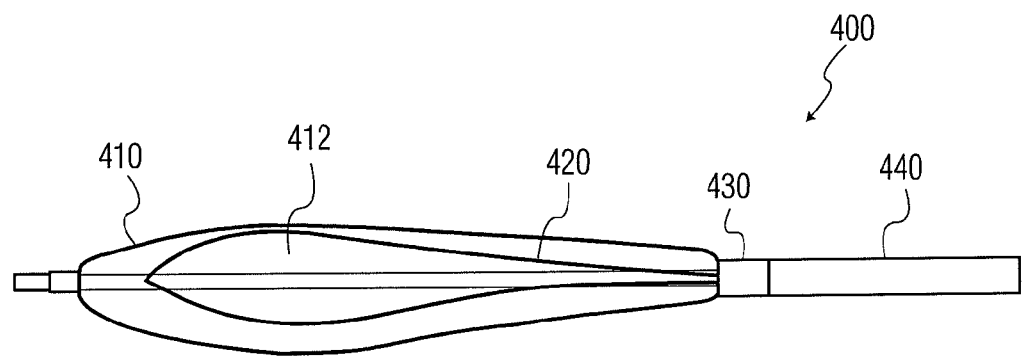
Figure 4C:
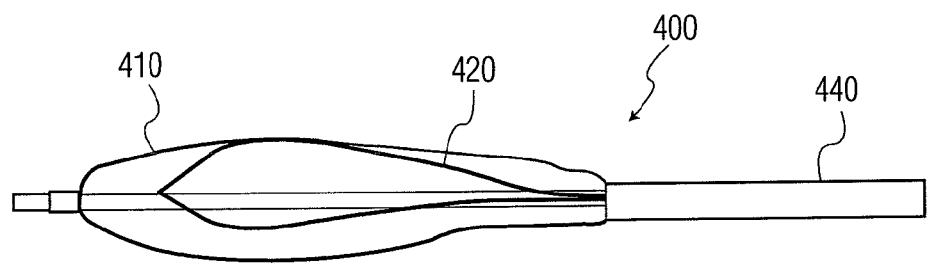
Figure 4D:
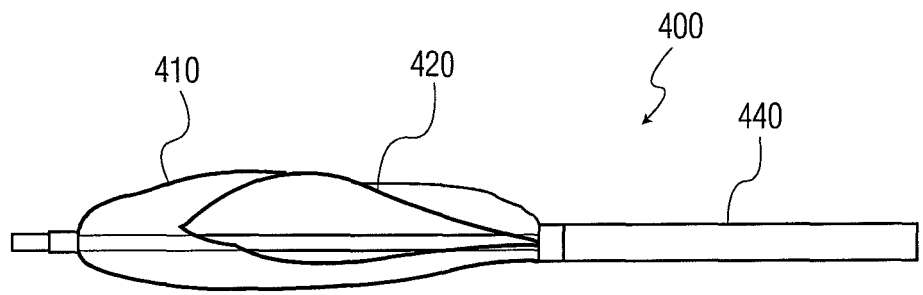
Figure 4E:
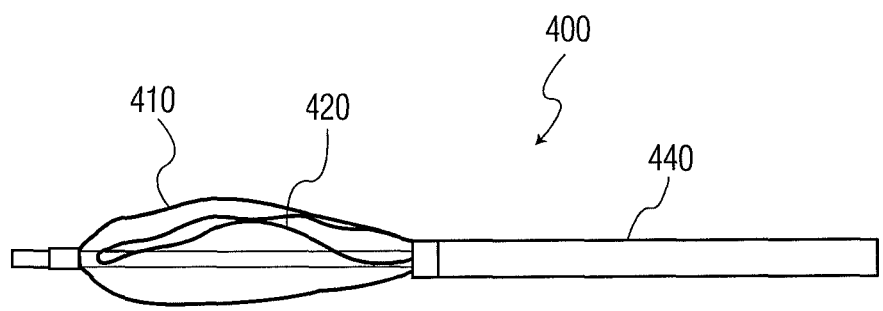
Figure 4F:
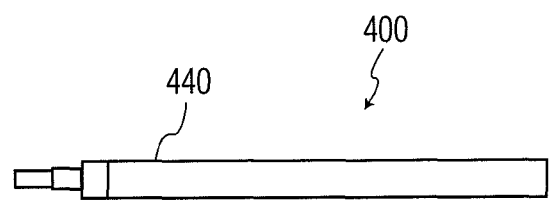

In FIG. 4B, the apparatus 400 has been partially collapsed (e.g., to trap particles in the filter 412). In FIGS. 4C-4F, the filter 412 and perimeter wire 410 are shown at various stages of retraction into the sheath 440. Upon full retraction, particles trapped in the filter 412 are contained within the sheath and removed (e.g., from within a blood vessel) upon removal of the catheter type apparatus 400.

FIGS. 5A-5C show portions of respective filter material, as may be implemented in connection with one or more embodiments. Example dimensions of respective holes and spacing therebetween are shown in each of the figures, by way of example with the understanding that various hole sizes and spacing are implemented to suit different embodiments. At FIG. 5A, a filter material 510 is shown with holes (including hole 512 labeled by way of example) with a relatively high density of holes and related porosity. At FIG. 5B, a filter material 520 is shown with holes (including hole 522 labeled by way of example) with a lower density than that shown in FIG. 5A. FIG. 5C shows a filter material 530 with holes (including hole 532 labeled by way of example) with a density between that shown in FIGS. 5A and 5B. These respective hole densities may be implemented with filters as described herein, such as with higher-density holes provided where the filter passes fluid, and with lower-density holes provided where the filter conforms to a vessel sidewall. As such, a varying degree of permeability of filter material can be attained.

Holes as shown in FIG. 5 may be formed using one or more of a variety of approaches. In some embodiments, the holes are drilled, with a thickness of the filter material set to accommodate such drilling. In other embodiments, a mesh or woven type material is used for the filter. In connection with these and other embodiments, it has been discovered that respective thicknesses of materials facilitate drilling while mitigating issues with regard to the passage of fluid, such as fluid including red blood cells. One such material that may be implemented in this regard is a polyurethane-on-paper film, such as ArgoMed or ArgoMedPLUS 18411 film available from Argotec of Massachusetts.

Figure 6:
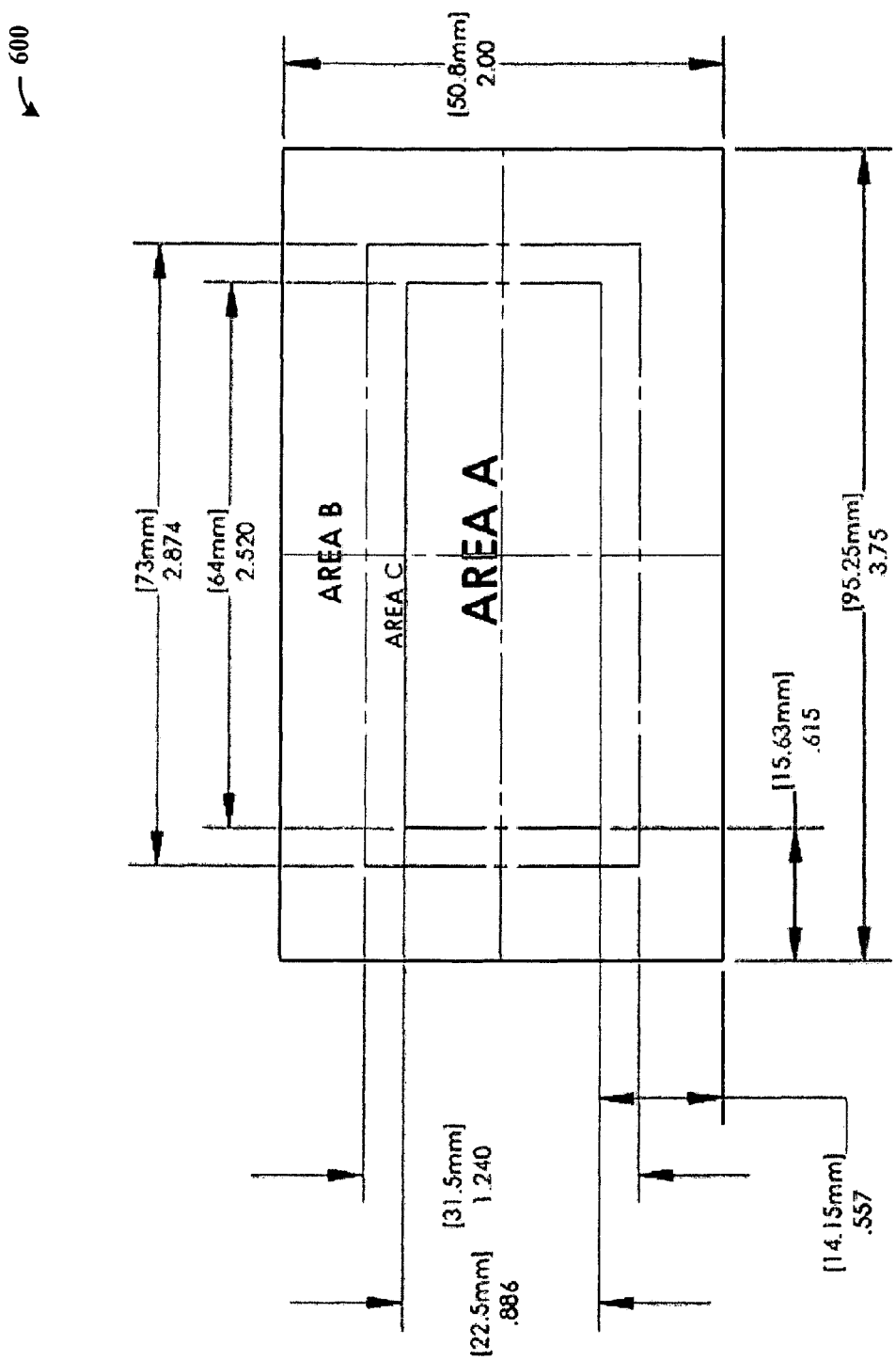
FIG. 6 shows a filter with respective regions having differing porosity characteristics, in accordance with another example embodiment.

FIG. 6 shows a filter 600 with respective regions having differing porosity characteristics, in accordance with another example embodiment. Specifically, regions labeled area A, area B and area C are implemented with respective hole/opening porosities. In some embodiments, area A includes a filter material as shown in FIG. 5A, area B includes a filter material as shown in FIG. 5B, and area C includes a filter material as shown in FIG. 5C.

Figure 7:
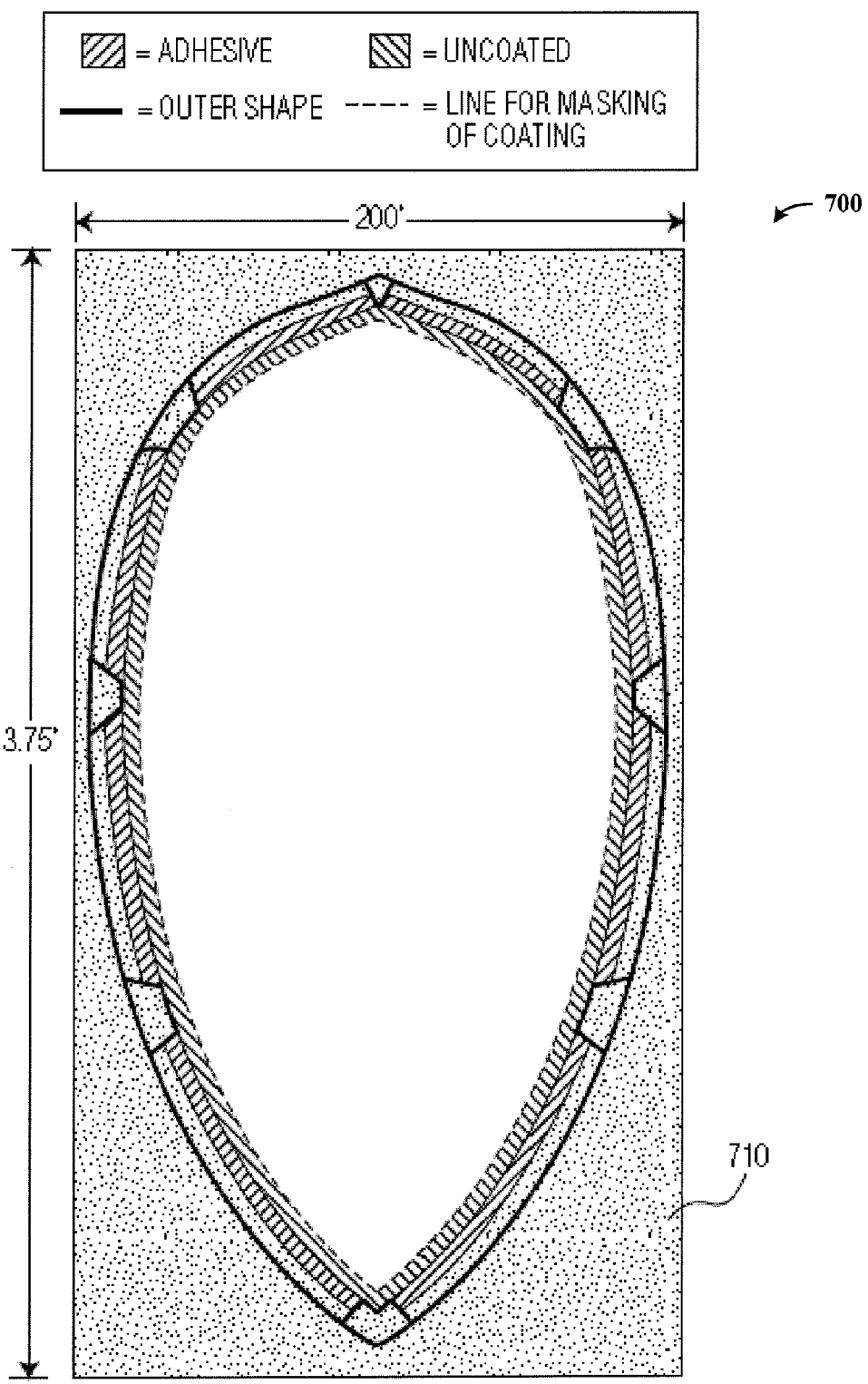
FIG. 7 shows a filter, in accordance with another example embodiment.

FIG. 7 shows a filter 700, in accordance with another example embodiment. The filter 700 may, for example, be used in a manufacturing process for forming a filter coupled to a perimeter wire. This coupling and arrangement of components facilitates expansion of the filter to conform to a vessel sidewall, and facilitates collapse of the filter to trap particles therein. In some implementations, the filter 700 is implemented in accordance with the hashed lines as shown, with an adhesive region and an uncoated region, with dashed lines representing masking for such a coating and a perimeter shown via solid line.

Figure 8:
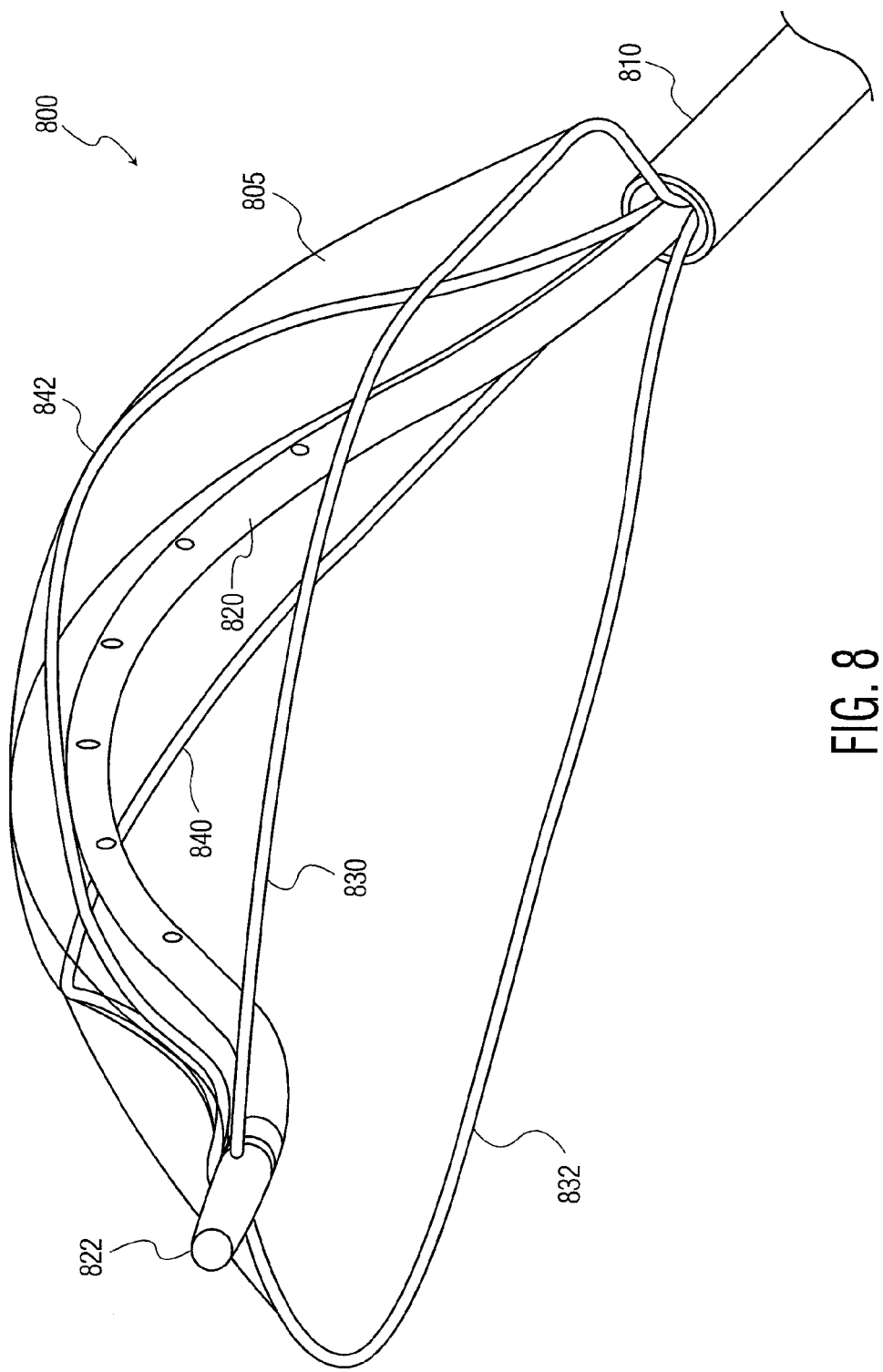
FIG. 8 shows a catheter apparatus, in accordance with another example embodiment.

FIG. 8 shows a proximal end portion of a catheter-type apparatus 800 for insertion into a patient, in accordance with another example embodiment. The apparatus 800 includes a filter 805, and an outer sheath 810 having a backbone type shaft 820 extending from a proximal end of the sheath. The backbone-type shaft 820 extends through the outer sheath to a distal end at which the shaft may be manipulated externally. Perimeter wires 830 and 832 are connected to an end 822 of the shaft 820, and extend into the sheath 810 to the distal end of the catheter, where the wires can also be manipulated externally. Optional wires 840 and 842 are also shown, connected to the backbone type shaft 820, and operable to provide shape to the filter 805. The backbone operates to provide a "C" type shape that facilitates shaping of the filter. By way of example, the backbone is shown with openings therein, which may be used to pass fluid into or out of the area in which the apparatus 800 is used.

The following discussion refers to various embodiments involving a filter apparatus and directed to one or more of protecting, capturing, filtering, aspirating, and diverting and trapping embolic particulate matter from traveling freely within the vascular arteries and the associated side branches while continuing to allow blood to flow freely and safely of emboli. These embodiments may, for example, be implemented with those described above and/or shown in the figures, such as with the catheter-based apparatus of FIG. 1 and/or the approaches shown in FIGS. 3A-3E. The devices can also be implemented for ease of delivery, deployment, expansion, visualization under x-ray and angiography, placement and adjustment, and retrieval/retraction through a single access point. Further, various embodiments herein refer to a filter or other component such as a mesh or fabric, which may be implemented as the EPCD and/or as part thereof. As such, various embodiments may be implemented using different approaches described using these and other terms, with other related terms.

The device delivery wire and mechanism itself can be made of various types of metal, fabric and or plastic materials and a wide range of wire, porous materials or mesh sizes. The total overall length of the device may have a range of lengths from as short as, e.g., 60 cm to 300 cm or greater, in length with possible placement of radiopaque markers at proximal, distal, medial, and lateral points within and about the frame and structure of the device. The EPCD frame or primary structure may be constructed of a nitinol, cobalt alloys, stainless steels, various polymers, PTFE, polyurethane, various plastics, bio-resorbable materials or any combination thereof.

The frame itself has one or more of a variety of geometric designs and mechanisms, such as diamond, kite, oval, leaf, pear, or similar geometric shape having a uniform sealing frame and edges for secure wall apposition and arch anatomy or between one or more points of primary contact distally, laterally, superior, inferior, and proximally, as may be implemented in one or more embodiments. In some implementations, the proximal origination of the frame evolves from one primary point of the delivery system so that it is easily deployed and recaptured. The shape of the distal points may be similar to that of a diamond or possibly two asymmetric elongated triangles or variation thereof, and function in a motion similar to how jaws open and close, opening and closing, edges overlapping, entrapping, or sealing or meeting flush, or some other opening and closing mechanism. In some implementations, the single backbone wire, hollow for transfer of wires or solid for support, with supporting frame and mesh forms the shape of one or more of an oval, kite, pear, or similar geometric shape and functions in a motion that would form and seal (or about seal) aspects within the anatomy of the aortic arch.

In one particular embodiment, a filter frame is as follows. The frame is from 2.5" to 6" in length, and the width in closed position is from 0.100" to 0.250." The width when expanded varies from 0.500" to 3.00" depending on anatomy the device is placed into. In the closed position (prior to expansion), the device fits into a 6-10fr delivery sheath or greater. The frame may be of a single layer of braided mesh, fabric or other porous material, and may include a double layer or multilayer design. The frame may have two layers of wire or plastic braid with a layer of material encapsulated between the two layers. The frame may be wire only for outer shape with braid, mesh or other porous material placed over the top of a skeletal frame, such as a kite structure with frame and material over it.

The device can be built in various configurations to suit particular embodiments, which may include one or more of: fixed wire tip, rapid exchange design, over the wire design, or a combination thereof. In some embodiments, the frame is all Nitinol or other metal, all plastic, or a combination of both. The radius will adjust to fit Aortic Arch of various anatomies. A center wire or wire/catheter with lumen operates as a back-bone of the device and allows the device to hold in top of aortic arch and have enough strength to remain in position under cardiac output flow and blood pressure conditions. This back-bone will also allow for the transfer of fluids, drugs, and other materials, such as for injection or aspiration. The devices herein can be made with multiple sizes accommodating a wide range of aortic arches, types, and/or small anatomy of an infant or adolescent.

The filter or porous membrane material of the EPCD device may be constructed of nitinol, cobalt alloys, polyurethane, stainless steels, various polymers, PTFE, various plastics, bio-resorbable materials or any combination thereof. For example, polymer blends such as a FEP/ePTFE (fluorinated ethylene propylene/expanded polytetrafluoroethylene) composite material may be implemented in this regard. The material of the membrane and the frame size itself would range in size and dimension to allow continuous blood flow and adequately cover the vessel walls in a concentric or eccentric fashion to protect and cover the major vessel branches and collateral side branches once deployed.

The filter or porous membrane deflects, detains, and or captures embolic debris, and may be made of a material that includes a drug coating such as heparin, thrombolytic drugs or anticoagulant drugs, and may include a material that attracts particulates that are desirably filtered. In some implementations, the backbone wire and mesh frame are ported to facilitate the delivery of drugs or other materials, such as anti-coagulants.

Other aspects are directed to stabilizing and securing a filter as described herein in a particular vascular anatomy, such as the aortic arch or other vascular tissue, and may include shapes relating to one or more of a wind sail, kite, or other geometric shape. The geometric shape of the material of the filters discussed herein can be implemented to seal and configure to the natural shape of a vessel wall as blood pressure and blood flow pump through the vessel, with porosity that facilitates ample blood flow both through the filter into openings secured as well as past the filter in bypassing the openings. This mechanism and geometric shape of the backbone wire or mesh frame may operate in a manner similar to how wind blows into a sail, parachute, kite or even the shape of a dome or half bubble, circle, oval, or ball, such that the mechanism presents a configuration which is curved, uniform and adapts to the walls of the vessel. In some implementations, the device takes advantage of fluid pressure to assist with placement and/or securement. The points of contact allow enough pressure to secure the filter in place and to incorporate wall apposition that would create a tight seal along and around the edges of the frame and ends of the device to mitigate or prevent emboli and/or thrombus from leaking/escaping behind or around the circumference and proximal or distal ends of the device and into unwanted vascular arteries and anatomy.

In various embodiments, the backbone (the central beam or wire, tubing or catheter body) is made with a strength and shape that allows the device to be held firmly against the top of the Aorta. The capture filter, basket or frame is then expanded from the back bone of the device and can conform to various aortic shapes along with covering one or more branches in the area once in position. The device facilitates deployment with torque, pushing, and tracking of the device into desired position, prior to expanding the capture portion of the device. This will allow for position and control in placing the device, which can be done prior to picking up all the forces that will come when the basket is expanded.

In some implementations, the backbone is shaped to conform to the top of the aorta. The front or distal portion of the device is specifically formed to hug tightly or push against the Aorta wall so that no blood flow can get between the device and the wall that would cause the device to be pushed away from the wall. The frame is shaped so that the outer edges of the frame where formed to push into the aorta.

In other embodiments, a filter frame and membrane distal and proximal ends and/or right and left edges can be collapsed to create a conical/funnel touching or overlapping configuration for capturing, aspirating, and filtering emboli in combination with the delivery and retrieval system, and continuing to allow for catheter use and exchange of equipment. The back bone and the distal and proximal ends of the device move independently of each other, when the back bone is pushed forward it causes the frame to expand into a larger radius. When the back bone is pulled back, it causes the frame to collapse and the outer edges of the frame are drawn in capturing anything that is in or on the inside of the frame. Various such embodiments are shown in the figures and in Appendix 1. For instance, edges may overlap when closed. Once closed, the device can then be pulled back into the delivery sheath with all the particulate still captured in the basket frame.

In some implementations, a frame is attached or fixed at the one end so proximal and distal ends can be moved relative to each other allowing expansion of the filter and device. This movement may facilitate sliding of the filter on a fixed deployment wire, aiding in both deployment of the device and the constraining of the filter/device for removal. In some implementations, radiopaque markers are distal, medial, and proximal and/or where appropriate to facilitate placement. The frame and wire itself may be implemented as rapid exchange, fixed tip or over-the-wire in design and mechanism. The backbone and frame can move independently of each other, the frame can be expanded when out of the sheath or closed down prior to being pulled into the sheath.

In some embodiments, a radiopaque (bumper and stopper) marker is located approximately at the distal end of a wire to prevent the distal portion of the frame from sliding back out and off the wire. When the filter is constrained, the sliding portion of the device (frame) can be pulled back with the filter in closed position. Once the device begins to be deployed, the frame starts to slide back away from the stopper while expanding into the vessel. Wall apposition of the device can be controlled, secure, and stabilized in an atrumatic matter by the frame and filter membrane.

In some embodiments, the filter is preloaded into a sheath, such as a pin and pull sheath, or other deployment and retrieval sheath or catheter. It can be loaded at time of use or could pre-loaded into the proprietary delivery system (e.g., having an outside diameter of approximately 6 French or greater). The delivery sheath may be constructed of a proprietary braided or non-braided PTFE material or other material, with a radiopaque tip and long shaft approximately 75 cm and 110 cm or greater in length for adults, with smaller dimensions for children. The device and delivery wire may thus be implemented with a lock, stop, and stabilize feature to assure little if any migration of the filter during the introduction and removal of devices.

In some embodiments, the frame and design also functions to stabilize and avoid migration of the EPCD system. Further to the membrane geometric shape and design, the collapsible lateral sides, and/or distal and proximal ends can be retrieved/collapsed to create a funnel/filter/conical configuration for aspiration, capturing and filtering emboli. Capturing the EPCD device would also include a delivery sheath and catheter or a secondary retrieval system of equal or greater French size.

In some embodiments, the delivery and retrieval sheath have a pressure lumen, with room for other tools after the filter is deployed, to passed/introduce and accessed to a target site. Such tools may include, for example, diagnostic catheters, aspiration catheters, or other adjunctive devices. The frame of the EPCD may be implemented with a porous material that covers the frame, thereby allowing continuous blood flow, preventing and avoiding unwanted embolic particulate matter to travel into or freely within the vascular vessels or associated side branches. In some implementations, the porous material captures embolic particulate matter as small as 60 to 180 microns.

The filter size may include one or more sizes and numbers of wire (PPI—Picks Per Inch), and may use porous fabric, polymer porous fabrics, and layers moved or positioned relative to each other to create different size porous/holes in the filter. The frame of one or more EPCDs as described herein may be either external of the filter or interwoven within the filter. The filter can either be positioned between the two braided layers or attached to the outer surface of the braid or frame. The EPCDs may include nitinol, stainless steel or other wire materials to include all kinds of wire sizes, multiple wires and PPI of the wires. The filter could also include a plastic mesh and/or fabric materials that are part of a basket or capture area of the device.

Based on different anatomies and applications, the EPCDs as described herein could be implemented using a broad-sized matrix, both in length of the frame and diameters. For instance, the frame length may vary from 0.5 cm up to 20 cm or greater, and the diameter and opening of the distal points may vary between 5 mm to 80 mm or greater. These approaches may allow for ample coverage of all arterial lumens of the greater arch vessels or aorta if necessary. Such approaches may be implemented to facilitate coverage of various arch classification types such as I, II, and III, and arch anomalies and variables such as a Bovine Arch.

The backbones/shafts described herein may be implemented using one or more of a variety of approaches. In some implementations, the backbone wire and mesh frame are operable to deflect in function so that the wire and mesh frame control the arch height and dimension of an EPCD, allowing the EPCD to fit various patient anatomy and sizes. In various embodiments, a backbone includes shapeable metal tubing, wire, or a catheter type shaft. The backbone holds the device tight against the top of the aorta, and is shaped to hold position in the aorta. The backbone facilitates in torque and positioning the device, and moves independently of the basket either on the proximal or distal end, which facilitates expansion and collapse of the filter. In some implementations, the backbone wire and mesh frame delivery wire proximal and distal connectors operate to move relative to each other, facilitating control of the width/size of the filter.

Various embodiments are directed toward protecting a patient from ischemic stroke during coronary and heart valve procedures by mitigating or blocking the passage of embolic particulate matter from entering the neurovascular arteries, and protecting the peripheral arteries and extremities. Other embodiments are directed to protecting patients from embolic induced ischemia in the peripheral vascular, coronary vascular or other vascular beds. This approach can be used in TAVI procedures but can also be used in any other procedure that requires distal protection.

Filter devices as discussed herein are implemented in one or more of a variety of manners. In some embodiments, a catheter-type filter device is placed via trans-catheter, trans-apical, or surgical cut down through most all vascular access vessels such as the right common femoral or left common femoral artery and/or brachial approach through the left or right subclavian arteries. The devices can be implemented as a temporary device in conjunction with a procedure that may dislodge or displace plaque, atheroma or thrombus that can travel within the vascular system. For instance, the devices and approaches can be used in the aorta and to protect the neurovasculature from ischemic stroke or transient ischemic attacks. Further to the proprietary frame and membrane design, the lateral sides and distal or proximal ends could be retrieved/collapsed to create a funnel/filter/conical shape configuration for capturing, aspirating, and filtering emboli traveling into the lower extremities.

In some implementations, a delivery device wire as described herein ranges from 0.014 inch to 0.035 inch, or greater, with an integrated and designed frame and structure that may include a geometric/asymmetrical/symmetrical porous membrane. In various embodiments, the geometrical and asymmetrical/symmetrical porous membrane is implemented with a consistent spacing pattern, or with an inconsistent spacing pattern depending on the anatomy and the need to curve/collapse/deploy and retrieve the device. The number of cells and/or weaves and/or geometric spaces per device is varied in some embodiments, based on the amount of area needed to expand and cover with the vascular anatomy.

Various geometric patterns include spaces or cells with a porous material or wire mesh weave connecting them together such as a nitinol mesh or weave, stainless steel mesh or weave, a polymer mesh or weave, a PTFE mesh or weave, a plastic mesh, polyurethane mesh or weave or a combination thereof. The porous material is implemented with a size that facilitates passing of red blood cells and capture of embolic particulate matter.

In some implementations, after gaining access via standard percutaneous technique or a cut down technique, an access needle is placed and a guide wire and short sheath introduced into a patient. A diagnostic wire is then exchanged and introduced. A diagnostic catheter is then introduced and the diagnostic wire removed. An arterial gram is taken to verify arterial and anatomical landmarks for proper device positioning and deployment. An exchange length wire is then introduced and the diagnostic catheter removed. A filter device as discussed herein is prepped, ready to be advanced into the vessels of the aorta and then positioned in and within the ascending aorta, great aortic arch, and descending aorta. The device (e.g., preloaded in a peel-away sheath, or pin and pull sheath, or retrieval and deployment sheath, or manually loaded) is then loaded on the wire either as a rapid exchange or over-the-wire system and introduced into the sheath and advanced to the end of the sheath that is currently positioned in the aorta. The wire tip can be made soft and shapeable to accommodate different anatomies and minimize any vessel trauma or breaking free of emboli. Once the device positioning is confirmed, the sheath, the pin and pull sheath, or proprietary retrieval and deployment sheath may be removed from while still in the original sheath.

At this point the EPCD device is ready for deployment. Using the radiopaque positioning markers for orientation and making sure that the wire is oriented on the greater curve of the arch, as may be implemented in the following examples:

EXAMPLE 1

Using the peel away sheath, a peel away portion of the sheath is removed and begin the sheath is pulled back with one hand keeping the EPCD wire stable. Peeling the sheath back will expose the EPCD and allow for the geometrical frame and membrane design to take shape and contour to the aortic arch.

EXAMPLE 2

Using the Pin and Pull sheath, the sheath is pulled back while keeping the wire stable, to expose the filter and allow for the geometrical frame and membrane design to take shape and contour to the aortic arch.

EXAMPLE 3

Using the retrieval and deployment sheath, the delivery system is engaged following the delivery device steps which will expose the filter and allow for the geometrical frame and membrane design to take shape and contour to the aortic arch.

EXAMPLE 4

Using the manual loaded method, the device is loaded into a delivery sheath or catheter and pushed to position the device in place, followed by similar steps as the pin and pull method to expose the filter and allow for the geometrical frame and membrane design to take shape and contour to the aortic arch.

Once the procedure (e.g., coronary surgery, valve replacement surgery) is completed, the device can be removed. Any embolic particulate matter that was captured or remaining can be filtered, aspirated, and removed using and following the retrieval step methods. Depending on the size, length or diameter of the device, it may take a larger sheath than the original sheath; use of a proprietary retrieval system, or an aspiration and extraction device to remove any emboli prior to removing/retrieving the device.

Using a retrieval sheath, remove the original sheath and advance a larger sheath into the descending aorta up to the most proximal end and remove the dilator. Once the dilator is removed, advance the sheath over the first segment making sure that it is collapsing into the advancing sheath; continue until the entire device is inside the sheath. At this point it is safe to remove both the wire and sheath from the patient.

Various other embodiments as described herein and/or referenced in connection with the claims may be implemented together with other embodiments herein and/or with the provisional patent applications referenced above.

Based upon the above discussion and illustrations, those skilled in the art will readily recognize that various modifications and changes may be made to the various embodiments without strictly following the exemplary embodiments and applications illustrated and described herein. For example, different types of materials may be used for the various components herein, and other manners in which to expand/collapse mesh-type structures with similar effect can be implemented. Additional shafts may be employed to separately move components of the filter material as discussed herein, such as by employing respective shafts to independently manipulate respective perimeters of the filter material, to conform the shape thereof. In addition, the various methods described herein may be implemented with different types of arteries, valves and tissue, as well as different types of live beings. Such modifications do not depart from the true spirit and scope of various aspects of the invention, including aspects set forth in the claims.

What is claimed is:

1. An apparatus comprising:
   an outer catheter extending from a proximal end to a distal end;
   a first shaft extending through the outer catheter from the proximal end to the distal end and being configured and arranged to move within the outer catheter, the first shaft having an end portion configured and arranged to retract within the proximal end;
   a second shaft configured and arranged to move relative to the first shaft and having an end portion that extends beyond the end portion of the first shaft, at least a portion of the second shaft being configured and arranged to retract into the outer catheter;
   a third shaft extending through the outer catheter, wherein the second shaft includes a fixed portion connected to the third shaft; and
   a filter configured and arranged to pass human red blood cells and to mitigate the passage of particles having a dimension larger than the human red blood cells, the filter having a perimeter structure that is connected to the second shaft, the filter being configured and arranged with the first, second and third shafts to
      expand to a first state in response to a portion of the second shaft being in a first position relative to the first shaft and a movable portion of the third shaft being extended toward the fixed portion of the second shaft, the filter having a dimension in the first state that is wider than a cross-sectional area of the outer catheter, and the filter having a surface area portion in the first state that is configured and arranged to cover an opening in a sidewall of vascular tissue and conform to portions of the sidewall around the opening, with the perimeter structure in an oblong shape, and
      collapse to a second state in response to the movable portion of the third shaft being retracted away from the fixed portion of the second shaft and the second shaft being manipulated to a second position in which the portion of the second shaft is manipulated relative to the first shaft, the filter and outer catheter being configured and arranged to facilitate retraction of the filter into the outer catheter in the second state.

2. The apparatus of claim 1, wherein the third shaft is connected to the first shaft and the end portion of the first shaft is an intermediate end portion operable to retract into the outer catheter.

3. The apparatus of claim 1, wherein
   the filter includes a porous material exhibiting variations in porosity at different portions of the filter, and
   the filter is configured and arranged with the first and second shafts to conform the surface area portion to the sidewall by conforming a majority of a surface of the filter to the sidewall in an oblong shape defined by the perimeter and having an elongated dimension that extends in a longitudinal direction along the sidewall.

4. The apparatus of claim 3, wherein the filter includes
   a first portion of a first porosity, the first portion being configured and arranged to conform to vessel sidewalls around the opening in response to fluid pressure, and
   a second portion of a second porosity that is higher than the first porosity, the second portion being configured and arranged to pass the human red blood cells through the opening in sidewalls of the vessel to which the first portion is conformed.

5. The apparatus of claim 3, wherein the filter includes at least one marker configured and arranged to identify the variations in porosity.

6. The apparatus of claim 1, further including a secondary frame connected to the second shaft and connected to the filter, the secondary frame configured and arranged with the second shaft and the filter to shape the surface area of the filter as a dome-type shape with the perimeter of the filter forming an exposed edge of the dome and being coupled to the second shaft, and with the secondary frame coupled to and supporting a domed portion of the filter extending away from the exposed edge, the dome-type shape being configured and arranged to conform to the sidewall of the vascular tissue while leaving a majority of a cross-section of a portion of the vascular tissue in which the filter is deployed unobstructed.

7. The apparatus of claim 1, wherein
   the filter has first and second end portions respectively connected to the end portions of the first and second shafts,
   the second shaft extends between the first and second end portions of the filter along a central portion thereof, and is configured and arranged to
      expand the filter by causing respective portions of the perimeter structure, at edges of the filter and on opposite sides of the second shaft, to spread apart from one another,
      collapse the filter by causing the respective portions of the perimeter structure to curl and overlap.

8. The apparatus of claim 1, wherein
   the distal end of the outer catheter is configured and arranged for insertion into human vascular tissue,
   the second shaft is configured and arranged to extend from the distal end of the outer catheter into the vascular tissue, and
   the first shaft, second shaft and filter are configured and arranged to, with the second shaft extending from the distal end of the outer catheter into the vascular tissue, expand the filter to the first state, position the filter onto a sidewall of the vascular tissue, and cover an opening into at least one artery connected to the vascular tissue with the surface area of the filter conforming to portions of the sidewall around the opening, in response to the portion of the second shaft passing into the first shaft, and collapse the filter to the second state in response to the portion of the second shaft passing out of the first shaft.

9. The apparatus of claim 1, wherein the first shaft, second shaft and filter are configured and arranged to capture particles in the filter when collapsing the filter to the second state, and to withdraw the collapsed filter with the captured particles into the outer catheter.

10. The apparatus of claim 9, wherein the first shaft, second shaft and filter are configured and arranged to trap a preponderance of particles that are in contact with the filter when the filter is collapsed to the second state.

11. The apparatus of claim 9, wherein the first shaft, second shaft and filter are configured and arranged to trap substantially all particles that are in contact with the filter when the filter is collapsed to the second state.

12. The apparatus of claim 1, wherein the distal end of the outer catheter is configured and arranged for insertion into a human aortic arch, the second shaft is configured and arranged to extend from the distal end of the outer catheter into the aortic arch, and the first shaft, second shaft and filter are configured and arranged to, with the second shaft extending from the distal end of the outer catheter into the aortic arch, expand the filter to conform to a sidewall of the aortic arch and to cover an opening into at least one artery in the aortic arch in response to the second shaft moving relative to the first shaft, with a portion of the filter conforming to the sidewall around the opening, while the filter is expanded, use the filter to pass red blood cells while capturing particles having a dimension larger than a largest dimension of the red blood cells, and collapse the filter to trap the captured particles and withdraw the collapsed filter with the captured particles into the outer catheter.

13. The apparatus of claim 1, wherein the filter has opposing surfaces and is configured and arranged with the first and second shafts to conform one of the surfaces to a wall of vascular tissue and cover at least one opening therein, with substantially all of one of the surfaces being in contact with the wall or extending over the at least one opening with portions of the filter being in contact with the wall immediately adjacent the opening.

14. The apparatus of claim 1, wherein at least one of the first and second shafts is configured and arranged with a passage therein that passes fluid between the proximal and distal ends of the outer catheter.

15. The apparatus of claim 14, wherein the first shaft extends along a central portion of the filter and is configured and arranged to pass anti-coagulant from the proximal end of the catheter and onto the filter, and is configured and arranged with the filter to disperse the anti-coagulant along the filter to mitigate collection of red blood cells in the filter.

16. The apparatus of claim 1, wherein the perimeter structure includes a flexible frame that extends along the perimeter of the filter.

17. The apparatus of claim 1, wherein the filter includes a semi-permeable membrane having at least one of a fabric and a fiber mesh, and has a frame extending along a perimeter of the at least one of the fabric and the fiber mesh.

18. The apparatus of claim 1, wherein the catheter is configured and arranged for insertion into a human aortic arch, and the first and second shafts are configured and arranged to conform the filter to a sidewall of the aortic arch and to cover an opening in the aortic arch leading into at least one artery.

19. The apparatus of claim 1, wherein the filter has at least one of: an anticoagulant that mitigates collection of red blood cells in the filter, and an attractant that facilitates coupling of the filter with particles carried by fluid passing through the filter.

20. The apparatus of claim 1, wherein the first shaft, second shaft and filter are configured and arranged to respond to the portion of the second shaft being retracted into the first shaft by expanding the filter to the first state and to cover at least one artery extending from the upper aortic arch.

21. The apparatus of claim 1, wherein one of the first and second shafts extends along and is coupled to a central portion of the filter, and the filter is configured and arranged with the first and second shafts to adjust a radius of the filter along the second shaft via movement of the second shaft relative to the first shaft.

22. A method comprising:

deploying a distal end of an outer catheter into vascular tissue, the outer catheter extending from a proximal end to a distal end, the outer catheter including a first shaft within the outer catheter and extending through the outer catheter from the proximal end to the distal end and being configured and arranged to move within the outer catheter, the first shaft having an end portion configured and arranged to retract within the proximal end, a second shaft configured and arranged to move relative to the first shaft and having an end portion that extends beyond the end portion of the first shaft, at least a portion of the second shaft being configured and arranged to retract into the outer catheter, a third shaft extending through the outer catheter, wherein the second shaft includes a fixed portion connected to the third shaft, and a filter configured and arranged to pass human red blood cells and to mitigate the passage of particles having a dimension larger than the human red blood cells, the filter having a perimeter structure that is connected to the second shaft;

manipulating the first, second and third shafts relative to one another to expand the filter to a first state by positioning a portion of the second shaft in a first position relative to the first shaft and extending a movable portion of the third shaft toward the fixed portion of the second shaft, the filter having a dimension that is wider than a cross-sectional area of the outer catheter in the first state, and covering an opening in a sidewall of the vascular tissue with the filter and with a surface area of the filter conforming to portions of the sidewall around the opening and with the perimeter structure in an oblong shape;

in the first state, using the filter to pass human red blood cells and to mitigate the passage of particles having a dimension larger than the human red blood cells;

manipulating the first and second shafts relative to one another to collapse the filter to a second state by retracting the movable portion of the third shaft away from the fixed portion of the second shaft and manipulating the second shaft to a second position in which the portion of the second shaft is manipulated relative to the first shaft; and in the second state, moving the first shaft relative to the outer catheter to retract the filter into the outer catheter.

23. The method of claim 22, wherein deploying the distal end of the outer catheter into vascular tissue includes deploying the distal end of the outer catheter into an aortic arch, manipulating the first and second shafts relative to one another to expand the filter to the first state includes expanding the filter to cover at least one artery connected to the aortic arch with the filter in the oblong shape defined by the perimeter structure and conforming to curvature of the sidewall around a longitudinal axis of the vascular tissue, and with the filter and the perimeter structure having an elongated dimension that extends in parallel with the longitudinal axis, and using the filter to pass human red blood cells and to mitigate the passage of particles having a dimension larger than the human red blood cells includes using the filter to pass the human red blood cells into the at least one artery, and to mitigate the passage of the particles having a dimension larger than the human red blood cells into the at least one artery.

24. The method of claim 22, further including using variations in porosity at different portions of the filter with flow of human blood to apply relatively high pressure to portions of the filter aligned with sidewalls of the vascular tissue around the opening and to apply relatively lower pressure to portions of the filter aligned with the opening.

25. The method of claim 24, wherein using the variations in porosity includes using a first filter portion of a first porosity to conform the filter to the sidewalls in response to fluid pressure, and using a second filter portion of a second porosity that is higher than the first porosity to pass the red blood cells through openings in sidewalls of the vascular tissue to which the first portion is conformed.

26. The method of claim 22, wherein manipulating the first and second shafts relative to one another to collapse the filter to the second state includes capturing particles in the filter, and wherein moving the first shaft relative to the outer catheter to retract the filter into the outer catheter includes withdrawing the collapsed filter with the captured particles into the outer catheter.

27. The method of claim 22, further including passing fluid between the proximal and distal ends of the outer catheter via at least one of: the catheter, the first shaft and the second shaft.

28. A capillary-based apparatus for filtering blood flow from the upper aortic arch of human vascular tissue, the apparatus comprising:

an outer catheter extending from a proximal end to a distal end, the distal end being configured and arranged for insertion into the upper aortic arch;

a first shaft extending through the outer catheter from the proximal end to the distal end and being configured and arranged to move within the outer catheter, the first shaft having an end portion configured and arranged to retract within the proximal end;

a second shaft configured and arranged to move relative to the first shaft within the outer catheter and having an end portion that extends beyond the end portion of the first shaft, at least a portion of the second shaft being configured and arranged to retract into the outer catheter;

a third shaft extending through the outer catheter, wherein the second shaft includes a fixed portion connected to the third shaft; and a filter having a filter material configured and arranged to pass human red blood cells and to mitigate the passage of particles having a dimension larger than the human red blood cells, the filter having a perimeter structure connected to the second shaft and having an end portion connected to the first shaft, the filter being configured and arranged with the first, second and third shafts to expand the filter material to a first state in which the perimeter structure is spread apart in an oblong shape having an elongated dimension that extends in a direction parallel with a longitudinal axis of the aortic arch, in response to a portion of the second shaft being extended out of the outer catheter toward the end portion of the first shaft and a movable portion of the third shaft being extended toward the fixed portion of the second shaft, the filter having a dimension that is wider than a cross-sectional area of the outer catheter in the first state and configured and arranged to conform to a sidewall of the vascular tissue and cover an opening therein, with a portion of a surface area of the filter conforming to portions of the sidewall around the opening, and collapse the filter material to a second state and trap particles on the filter therein, in response to the movable portion of the third shaft being retracted away from the fixed portion of the second shaft and the second shaft being drawn into the outer catheter and away from the end portion of the first shaft, the filter and outer catheter being configured and arranged to facilitate retraction of the filter with the trapped particles into the outer catheter in the second state.

* * * * *